(12) United States Patent
Olson

(10) Patent No.: US 10,568,702 B2
(45) Date of Patent: Feb. 25, 2020

(54) SYSTEM AND METHOD FOR RE-REGISTRATION OF LOCALIZATION SYSTEM AFTER SHIFT/DRIFT

(71) Applicant: ST. JUDE MEDICAL, CARDIOLOGY DIVISION, INC., St. Paul, MN (US)

(72) Inventor: Eric S. Olson, Maplewood, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 90 days.

(21) Appl. No.: 15/875,457

(22) Filed: Jan. 19, 2018

(65) Prior Publication Data

US 2018/0200003 A1 Jul. 19, 2018

Related U.S. Application Data

(60) Provisional application No. 62/447,987, filed on Jan. 19, 2017.

(51) Int. Cl.
*G06T 7/00* (2017.01)
*A61B 34/20* (2016.01)
(Continued)

(52) U.S. Cl.
CPC ............ *A61B 34/20* (2016.02); *A61B 5/0422* (2013.01); *A61B 5/0538* (2013.01); *A61B 5/062* (2013.01); *A61B 5/065* (2013.01); *A61B 5/6852* (2013.01); *G06T 7/0016* (2013.01); *G06T 7/60* (2013.01); *G06T 7/74* (2017.01); *A61B 18/1492* (2013.01); *A61B 2017/00694* (2013.01); *A61B 2017/00725* (2013.01); *A61B 2018/00011* (2013.01);
(Continued)

(58) Field of Classification Search
None
See application file for complete search history.

(56) References Cited

U.S. PATENT DOCUMENTS 6,233,476 B1 5/2001 Strommer et al.
6,690,963 B2 2/2004 Ben-Haim et al.
(Continued)

FOREIGN PATENT DOCUMENTS

WO WO-2008083111 A1 * 7/2008 ............... A61B 5/06

OTHER PUBLICATIONS

Semi-Automatic Basket Catherer Reconstruction from two X-ray Views, Zhong et al. Jan. 2015.*
(Continued)

*Primary Examiner* — Delomia L Gilliard
(74) *Attorney, Agent, or Firm* — Dykema Gossett PLLC

(57) ABSTRACT

A system and method are provided for determining one or more characteristics of a device. The system and method comprises initiating an algorithm to correct for shift and drift of a reference catheter (203), determining an initial shape and position of a portion of the reference catheter at time 0 when the algorithm is initiated (201), determining a current shape and position of the portion of the reference catheter at time t after the algorithm has been initiated (205), calculating a closest fit of the current shape and position of the portion of the reference catheter to the initial shape and position of the portion of the reference catheter by iteratively adjusting a set of solution parameters (209), and determining a minimal error solution parameter (211).

25 Claims, 12 Drawing Sheets

(51) Int. Cl.
*A61B 5/06* (2006.01)
*G06T 7/60* (2017.01)
*G06T 7/73* (2017.01)
*A61B 5/042* (2006.01)
*A61B 5/00* (2006.01)
*A61B 5/053* (2006.01)
*A61B 18/14* (2006.01)
*A61B 18/00* (2006.01)
*A61B 90/00* (2016.01)
*A61B 17/00* (2006.01)

(52) U.S. Cl.
CPC ............ *A61B 2018/00577* (2013.01); *A61B 2034/2051* (2016.02); *A61B 2034/2053* (2016.02); *A61B 2034/2061* (2016.02); *A61B 2034/2065* (2016.02); *A61B 2090/0812* (2016.02); *A61B 2562/06* (2013.01); *G06T 2207/10028* (2013.01); *G06T 2207/30021* (2013.01); *G06T 2207/30048* (2013.01)

(56) References Cited

U.S. PATENT DOCUMENTS

| | | |
|---|---|---|
| 7,197,354 B2 | 3/2007 | Sobe |
| 7,263,397 B2 | 8/2007 | Hauck et al. |
| 7,386,339 B2 | 6/2008 | Strommer et al. |
| 7,848,789 B2 | 12/2010 | Govari et al. |
| 2017/0273614 A1* | 9/2017 | Giphart ................ A61B 6/04 |

OTHER PUBLICATIONS

3D Robotic Catherer Shape Reconstruction and Localisation Using Appearance Priors and Adaptive C-Arm Positioning. Vandini et al. Jan. 2013.*
Automated Pointing of Cardiac Imaging Catherers. Loschak et al. May 2013.*

* cited by examiner

SYSTEM AND METHOD FOR RE-REGISTRATION OF LOCALIZATION SYSTEM AFTER SHIFT/DRIFT

CROSS-REFERENCE TO RELATED APPLICATIONS

This application claims the benefit of U.S. provisional application No. 62/447,987, filed 19 Jan. 2017 (the '987 application), which is hereby incorporated by reference as though fully set forth herein.

BACKGROUND a. Field

The present disclosure relates to a system and method for determining one or more characteristics of a medical device within a body, including the position of the device. In particular, the instant disclosure relates to a system and method that enable correction of drift and shift in position measurements in electric field based position and navigation systems.

b. Background

A wide variety of medical devices are inserted into the body to diagnose and treat various medical conditions. Catheters, for example, are used to perform a variety of tasks within the body including the delivery of medicine and fluids, the removal of bodily fluids, and the transport of surgical tools and instruments. In the diagnosis and treatment of atrial fibrillation, for example, catheters may be used to deliver electrodes to the heart for electrophysiological mapping of the surface of the heart and to deliver ablative energy to the surface among other tasks. Catheters are typically routed to a region of interest through the body's vascular system. In a conventional approach, an introducer is used to puncture the skin surface and a sheath having an inner diameter greater than the outer diameter of the catheter is threaded through the vasculature to a region of interest. The catheter is then moved longitudinally through the sheath to the region of interest either manually by a clinician or through the use of electromechanical drive systems.

Clinicians track the position of medical devices such as catheters as they are moved within the body so that, for example, drugs and other forms of treatment are administered at the proper location and medical procedures can be completed more efficiently and safely. Medical device navigation systems have been developed to track the position of medical devices within the body. These systems typically rely on the generation of electrical or magnetic fields and the detection of induced voltages and currents on position sensors attached to the medical device and/or external to the body. The information derived from these systems is then provided to a physician through, for example, a visual display.

For navigation and localization systems as described above, a reference electrode on a reference catheter can be used to determine a reference point within the heart. The reference electrode can be placed at a desired location to provide a stable reference point or origin for a navigation and localization system (e.g., parking a navigational reference catheter so that by moving a mapping catheter within a heart chamber coordinates may be acquired). In some instances the reference catheter can be positioned in the coronary sinus and constrained by the walls of the coronary sinus. The accuracy of the reference electrode is subject to various types of interference that can impact the accuracy of position measurements. For example, the level of electrical impedance in the patient body is not necessarily constant. The impedance can slowly drift or even undergo transient shifts due to, for example, a change in medication, saline loading, rhythm change, etc, which can lead to drift and/or shift in the detected position of the medical device. Further, the reference catheter may become dislodged during the procedure. Various methods have been proposed to mitigate potential drift or shift including the use of a fixed reference catheter with a reference electrode and bio-impedance scaling. Using only a single electrode can lead to problems if the catheter becomes dislodged from the position it was placed or if the reference catheter moves distally or proximally within the vessel where it was positioned. Bio-impedance scaling can correct some degree of shift/drift, but is not able to adequately correct shift/drift in all circumstances. These errors can be represented mainly by translational errors. Further, a single reference electrode is unable to address rotational and scale errors. The systems and methods described herein can alleviate these problems.

BRIEF SUMMARY

The present disclosure relates to a system and method for determining one or more characteristics of a device within a body. In particular, the instant disclosure relates to a system and method that enable correction of drift and shift in position measurements in electric field based position and navigation systems.

In one embodiment, a system for determining one or more characteristics of a device can comprise an electronic control unit. The electronic control unit can be configured to initiate an algorithm to correct for shift and drift of a reference catheter, determine an initial shape and position of a portion of the reference catheter at first time when the algorithm is initiated, determine a current shape and position of the portion of the reference catheter at second time after the algorithm has been initiated, calculate a closest fit of the current shape and position of the portion of the reference catheter to the initial shape and position of the portion of the reference catheter by iteratively adjusting a set of solution parameters, and determine a minimal error solution parameter.

In another embodiment of the disclosure, a method for determining one or more characteristics of a device can comprise initiating an algorithm to correct for shift and drift of a reference catheter, determining an initial shape and position of a portion of the reference catheter at time 0 when the algorithm is initiated, determining a current shape and position of the portion of the reference catheter at time t after the algorithm has been initiated, calculating a closest fit of the current shape and position of the portion of the reference catheter to the initial shape and position of the portion of the reference catheter by iteratively adjusting a set of solution parameters, and determining a minimal error solution parameter.

The foregoing and other aspects, features, details, utilities, and advantages of the present disclosure will be apparent from reading the following description and claims, and from reviewing the accompanying drawings.

DETAILED DESCRIPTION

Figure 1:
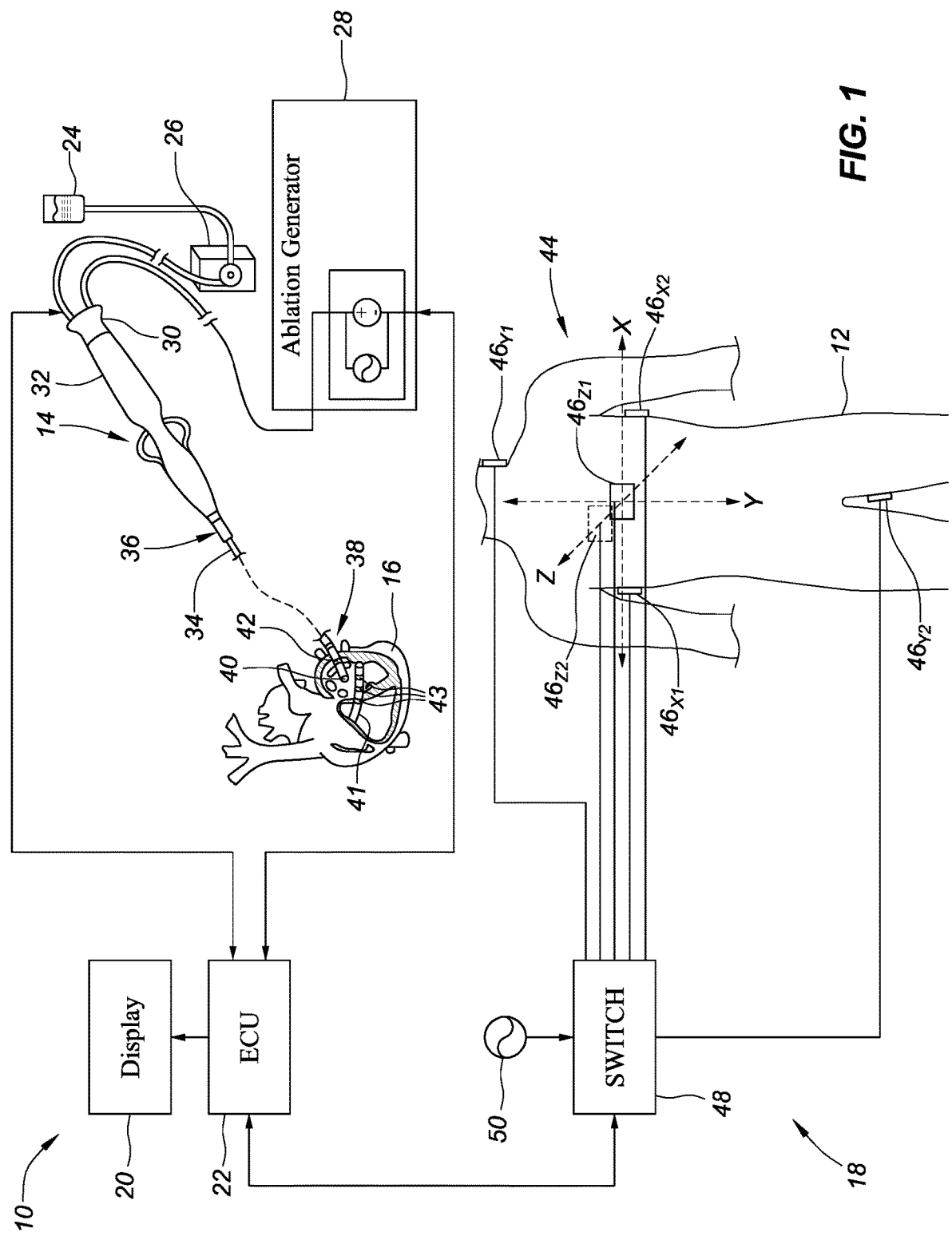
FIG. 1 is diagrammatic view of one embodiment of a system for determining one or more characteristics of a device electrode disposed on a medical device within a body in accordance with the present teachings.

Referring now to the drawings wherein like reference numerals are used to identify identical components in the various views, FIG. 1 illustrates one embodiment of a system 10 for determining one or more characteristics of a medical device within a body 12. In the illustrated embodiment, the medical device comprises a catheter 14 and, in particular, an irrigated ablation catheter for use in diagnosis or treatment of cardiac tissue 16 in body 12. It should be understood, however, that a system 10 in accordance with the present teachings may find application in connection with a wide variety of medical devices used within body 12 for diagnosis or treatment. Further, it should be understood that the system 10 may be used with medical devices used in the diagnosis or treatment of portions of body 12 other than the tissue 16. In the embodiment shown in FIG. 1, system 10 includes an electric field based positioning system 18 a display 20, and an electronic control unit (ECU) 22.

Catheter 14 is provided for examination, diagnosis and treatment of internal body tissues such as cardiac tissue 16. In accordance with one embodiment, catheter 14 comprises an ablation catheter and, more particularly, an irrigated radio-frequency (RF) ablation catheter. It should again be understood, however, that catheter 14 is provided for illustration only and that system 10 could be adapted for use with a variety of catheters including, for example, electrophysiology mapping catheters and intracardiac echocardiograph (ICE) catheters, as well as for use with other types of ablation catheters including those providing different types of ablation energy (e.g., cryoablation, ultrasound, etc.). Catheter 14 is connected to a fluid source 24 having a biocompatible fluid such as saline through a pump 26 (which may comprise, for example, a fixed rate roller pump, a peristaltic pump, or variable volume syringe pump with a gravity feed supply from fluid source 24 as shown) for irrigation. Catheter 14 is also electrically connected to an ablation generator 28 for delivery of RF energy. Catheter 14 may include a cable connector or interface 30, a handle 32, a shaft 34 having a proximal end 36 and a distal end 38, and one or more device electrodes 40, 42. Catheter 14 may also include other conventional components not illustrated herein such as a temperature sensor, additional electrodes, and corresponding conductors or leads.

Connector 30 provides mechanical, fluid and electrical connection(s) for conduits or cables extending from pump 26 and ablation generator 28. Connector 30 is conventional in the art and is disposed at the proximal end 36 of catheter 14.

Handle 32 provides a location for the physician to hold catheter 14 and may further provide a means for steering or guiding shaft 34 within the body 12. For example, handle 32 may include means to change the length of a guide wire extending through catheter 14 to distal end 38 of shaft 34 to steer distal end 38 and, thus, shaft 34. Handle 32 is also conventional in the art and it will be understood that the construction of handle 32 may vary.

Shaft 34 is an elongated, flexible member configured for movement within body 12. Shaft 34 supports electrodes 40, 42, associated conductors, and, in some embodiments, additional electronics used for signal processing or conditioning. Shaft 34 may also permit transport, delivery, and/or removal of fluids (including irrigation fluids and bodily fluids), medicines, and/or surgical tools or instruments. Shaft 34 may be made from conventional materials such as polyurethane and defines one or more lumens configured to house and/or transport electrical conductors, fluids, or surgical tools. Shaft 34 may be introduced into a blood vessel or other structure within body 12 through a conventional introducer sheath. Shaft 34 may then be steered or guided through body 12 to a desired location such as tissue 16 using guide wires or pull wires or other means known in the art including remote control guidance systems.

Device electrodes 40, 42 may be provided for a variety of diagnostic and therapeutic purposes including, for example, electrophysiological studies, catheter identification and location, pacing, and cardiac mapping and ablation. Electrodes 40, 42 may also be provided for use in determining the position of catheter 14 within body 12. In the illustrated embodiment, catheter 14 includes an ablation tip electrode 40 at distal end 38 of shaft 34 and one more ring electrodes 42 located proximal to the tip electrode. It should be understood, however, that the number, orientation, and purpose of electrodes 40, 42 may vary. As electrodes 40, 42 move within body 14, and within the electric field generated by system 18, the voltage readings from electrodes 40, 42 change thereby indicating the location of electrodes 40, 42 within the electric field and with a coordinate system 44 established by system 18. Electrodes 40, 42 communicate signals to ECU 22 through a conventional interface (not shown).

System 18 is provided to determine the position and orientation of catheter 14 and similar devices within body 12. System 18 may comprise a portion or all of the system made available under the trademark "ENSITE NAVX" by St. Jude Medical, Inc. and described, for example, in U.S. Pat. No. 7,263,397 titled "Method and Apparatus for Catheter Navigation and Location Mapping in the Heart," the entire disclosure of which is incorporated herein by reference. The system 18 is based on the principle that when low amplitude electrical signals are passed through the thorax, body 12 acts as a voltage divider (or potentiometer or rheostat) such that the electrical potential or field strength measured at an electrode such as one of device electrodes 40, 42 on catheter 14 may be used to determine the position of the electrode, and therefore catheter 14, relative to a pair of external measurement electrodes using Ohm's law and the relative location of a plurality of reference electrodes 43 on a reference catheter 41. The systems and methods described herein comprise determining the position of the plurality of reference electrodes 43 on the reference catheter 41. By determining the position of a plurality of the reference electrodes instead of using a single reference electrode as previously performed, the systems and methods described herein can provide an improved process to determine and correct for errors arising from shift, drift, rotational error, scale error, and dislodgement, among other errors. In the illustrated embodiment, the reference catheter can be located within a coronary sinus of the heart. In other embodiment, the reference catheter can be secured in other desired vessels as would be known to one of ordinary skill in the art. In one configuration, the system includes three pairs of measurement electrodes 46 that are placed on opposed surfaces of body 12 (e.g., chest and back, left and right sides of the thorax, and neck and leg) and form generally orthogonal x, y, and z axes. The system 18 also typically includes a reference electrode/patch that is typically placed near the belly of the patient and provides an impedance reference value and may act as the origin of the coordinate system 44 for the navigation system. In accordance with one aspect of the present teachings discussed in greater detail below, however, a virtual reference electrode within body 12 may replace the external reference electrode/patch as the origin of coordinate system 44 and, further, the impedance reference may be relocated and even be disposed within body 12 for improved compensation of drift and shifts. In yet other embodiments, a virtual reference electrode can be used in lieu of a single electrode position reference or in conjunction with a single electrode position reference. In another embodiment, a virtual reference electrode can be used to create a coordinate origin closer to the heart so that artifact motion from respiration or other sources do not cause large excursions from the coordinate origin. Sinusoidal currents can be driven through each pair of measurement electrodes 46 and voltage measurements for one or more device electrodes 40, 42 associated with catheter 14 are obtained. In other embodiments, the current driven through each pair of measurement electrodes can comprise an alternating or oscillating current. The measured voltages are a function of the distance of the device electrodes 40, 42 from the measurement electrodes 46. The measured voltages may be compared to a position reference such as the virtual reference electrode described in greater detail below and a position of the electrodes 40, 42 within the coordinate system 44 of the navigation system may be determined. In accordance with this exemplary system, system 18 may include measurement electrodes 46 (namely $46_{X1}$, $46_{X2}$, $46_{Y1}$, $46_{Y2}$, $46_{Z1}$, $46_{Z2}$) a switch 48, and a signal generator 50.

Measurement electrodes 46 are provided to generate electrical signals used in determining the position of catheter 14 within three-dimensional coordinate system 44 of system 18. Electrodes 46 may also be used to generate EP data regarding tissue 16. The EP data can comprise tissue impedance or other measurements. Electrodes 46 may comprise patch electrodes having a flexible substrate and which are affixed to the surface of body 12 using adhesives. Electrodes 46 are generally placed orthogonally on the surface of body 12 and are used to create axes specific electric fields within body 12. Electrodes $46_{X1}$, $46_{X2}$ may be placed along a first (x) axis. Similarly, electrodes $46_{Y1}$, $46_{Y2}$ may be placed along a second (y) axis, and electrodes $46_{Z1}$, $46_{Z2}$ may be placed along a third (z) axis. Each of the electrodes 46 may be coupled to multiplex switch 48. In one embodiment, the multiplex switch can comprise time multiplexing based on switching. In other embodiments, the multiplex switch can comprise frequency based multiplexing. ECU 22 is configured through appropriate software and/or hardware to provide control signals to switch 48 and thereby sequentially couple pairs of electrodes 46 to signal generator 50 in order to form active or driven electrode pairs. In other embodiments, the electrodes can be placed in other formations. Excitation of each active pair of electrodes 46 generates an electromagnetic field within body 14 and within an area of interest such as the heart. In some embodiments the excitation of each active pair can comprise excitation across orthogonal pairs of electrodes. In other embodiments, the excitation of each active pair can comprise excitation across other pairs of electrodes, including adjacent pairs of electrodes. Voltage levels at passive or non-driven electrodes 46 may be filtered and converted and provided to ECU 22 for use as reference values and, in particular, to establish a virtual reference electrode as discussed in greater detail below.

Display 20 is provided to convey information to a physician to assist in diagnosis and treatment. Display 20 may comprise one or more conventional computer monitors or other display devices. Display 20 may present a graphical user interface (GUI) to the physician. The GUI may include a variety of information including, for example, an image of the geometry of tissue 16, electrophysiology data associated with the tissue 16, graphs illustrating voltage levels over time for various electrodes 40, 42, and images of catheter 14 and other medical devices and related information indicative of the position of catheter 14 and other devices relative to the tissue 16.

ECU 22 provides a means for controlling the operation of various components of system 10 including catheter 14 and ablation generator 28 and switch 48 of system 18. ECU 22 may also provide a means for determining the geometry of tissue 16, electrophysiology characteristics of tissue 16 and the position and orientation of catheter 14 relative to tissue 16 and body 12. ECU 22 also provides a means for generating display signals used to control display 20. ECU 22 may comprise one or more programmable microprocessors or microcontrollers or may comprise one or more application specific integrated circuits (ASICs). ECU 22 may include a central processing unit (CPU) and an input/output (I/O) interface through which ECU 22 may receive a plurality of input signals including signals generated by ablation generator 28, device electrodes 40, 42 on catheter 14, and measurement electrodes 46 of system 18. The CPU and I/O interface of the ECU 22 is also configured to generate a plurality of output signals including those used to control and/or provide data to catheter 14, display 20, ablation generator 28, switch 48 of system 18, and generator 50 of system 20.

In accordance with the present teachings, ECU 22 may be configured with programming instructions from a computer program (i.e., software) to implement a method for determining one or more characteristics of a device electrode 40, 42 on a medical device such as catheter 14 with body 12. The program may be stored in a computer storage medium such as a memory (not shown) that is internal to ECU 22 or external to ECU 22, and may be pre-installed in the memory or obtained from a computer storage medium external to ECU 22 including from various types of portable media (e.g., compact discs, flash drives, etc.) or file servers or other computing devices accessible through a telecommunications network.

In one embodiment, where a reference catheter is used as a positional reference within a coronary sinus, a user can select an electrode present on a constrained portion of the reference catheter and then tell or otherwise signal to a system as described herein that the location where the electrode is positioned is stationary relative to the heart. The system can then keep the selected electrode stationary through the following process. To start the process of keeping the electrode stationary, the system determines:

$$\text{offset}_t = x(c)_t - x(c)_0$$

and $$y(e)_t = x(e)_t - \text{offset}_t$$

In the above equations, $x(e)_t$ is the raw location of the electrode e, at time t, and $y(e)_t$ is the transformed location of the same electrode via the use of the positional reference approach. Further, $x(c)_0$ is the position of the chosen positional reference electrode c at the time point, 0, when the positional reference was first set. For the electrode, c, at a location at some future time, t, it can be observed by plugging that location to the above equation the following equation results:

$$y(c)_t = x(c)_t - (x(c)_t - x(c)_0)$$

which further results in:

$$y(c)_t = x(c)_0$$

As seen in the above equation, the electrode, c, will remain fixed at the location $x(c)_0$ for all future time points. This location can then be used as a reference location that will remain fixed to build the rest of the electroanatomical map. The above process can work well for shift/drift that can be accounted for by a simple translation. However, there are deficits to using this method. There is no guarantee that the assumption that the reference catheter will remain fixed within the coronary sinus or other vessel throughout the course of an electrophysiology procedure. In some cases, the reference catheter will no longer remain fixed through motion of the heart or through manipulation of other catheters in the heart, which can cause the reference catheter in the coronary sinus or other vessel to become dislodged. A dislodgement of the reference catheter from the desired vessel can cause a shift of the coordinate system. This can be a problem, as this shift is what the reference catheter was intended to prevent. Moreover, the idea that all shift/drift can be accounted for by a simple translation, as mentioned above, is not strictly true. A shift/drift of the position measurement can incorporate varying modes of error. The shift/drift of the position measurement can be deformed with respect to a global scale, an axis-independent scale, rotation, skew, and morphing. The method described above using a single electrode cannot address these other modes of shift/drift.

The methods and systems disclosed herein are designed to be insensitive to catheter dislodgement as well as able to mitigate some degree of higher order error modes, such as rotation and scale errors. The methods and systems disclosed herein can utilize an entire catheter (or multiple electrodes from more than one catheter) to establish a positional reference to correct or modify errors caused by shift and/or drift instead of a single electrode. To utilize the method and systems described herein a reference catheter comprising a plurality of reference electrodes is placed at a reference location within the coronary sinus or other vessel(s), or other stable locations. The reference catheter can be placed into a confined space within the coronary sinus or other vessel which can limit the ability of the reference catheter to move after it has been placed in its reference location. A reference catheter in such a location is unable to move laterally and resists movement in the longitudinal direction due to frictional and other forces present on the catheter within the confined space of the coronary sinus or other vessel. By leveraging the length of the entire catheter, or a significant portion of the length of a catheter, and any reference electrodes along the chosen length of the catheter, the methods and systems described herein can correct for shift and/or drift. The methods and systems described herein can further correct for higher level modes of error, such as rotational and scale errors. Further, the methods and systems described herein can be tolerant to dislodgements. This can be accomplished by determining the best fit of the current sensed catheter shape to the shape of the catheter when the algorithm was initiated. The shape of the catheter can be determined by using the location of the reference electrodes on the catheter. As the reference electrodes are placed in a known configuration on the catheter, the determined location of the electrodes can be used. As the catheter is secured within the constraining vessel when the determination is first initiated, the catheter shape can be the shape of the constraining vessel, such as the coronary sinus for example. The current shape and/or position of the reference catheter can be represented as a cloud of points. Further, the original shape and/or position of the reference catheter can be represented by several different methods. These methods include a cloud of points, a shadow, surface geometry, a distance map, or other methods as would be known to one of ordinary skill in the art. The algorithm used in the methods and systems described herein can then find the closest fit of the current catheter shape and/or position to the original shape and/or position of the reference catheter. The algorithm can determine the closest fit by iteratively adjusting a set of registration parameters and evaluating the error of the solution. The error of the solution would be the quality of fit between the registered location of the current catheter position to the original reference shape. The registration parameters used by the algorithm can comprise at least one of translation, rotation, global scale, axis-independent scale, skew, and morphing. Each of the registration parameters can add errors to the solution. The errors from one or more of the registration parameters can generally be a fitness of the current shape and/or position to the original shape and/or position in terms of distance. The error can be a Euclidean norm error or a root-mean-square (RMS) error along the entire length of the catheter or along a portion of the catheter. In one embodiment, the Euclidean norm error can be calculated along the entire length of a portion of a catheter that is within a heart or other vessel of a patient. In another embodiment, the Euclidean norm error can be calculated along a subset of a portion of the catheter that is within a heart of a patient. In yet another embodiment, the Euclidean norm error can be calculated along a portion of the catheter that extends from a distal end of the catheter to a portion of the catheter adjacent the superior vena cava. After the Euclidean norm error has been converged by the algorithm to a minimal error, a set of solution parameters can be declared to be the optimum by the methods and systems disclosed herein and the set of solution parameters can be used to adjust the navigation system coordinates.

Figure 2A:
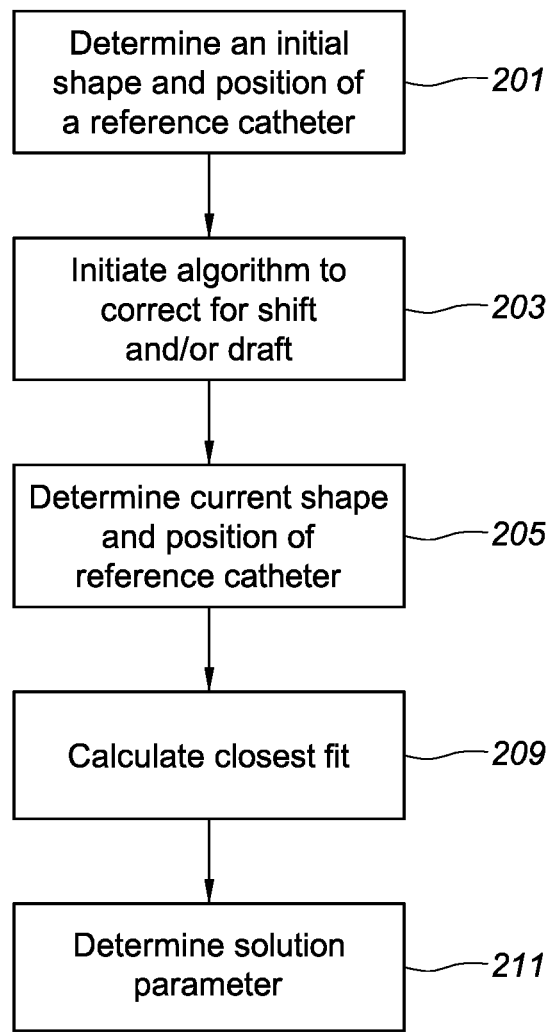
FIG. 2A is a flowchart illustrating one embodiment of a system for determining one or more characteristics of a device.

FIG. 2A illustrates a flow chart depicting one embodiment of a system for determining one or more characteristics of a device. The system can comprise an electronic control unit as described in FIG. 1.

Step 201 comprises determining an initial shape and position of the reference catheter. In one embodiment, a position of a plurality of reference electrodes on the reference catheter can be used to determine an initial shape and position of the reference catheter. In another embodiment, the location of the plurality of reference electrodes can be used to create a point cloud of the reference catheter. In yet other embodiments, the methods and processes described herein can be used to determine the initial shape and position of the reference catheter. A cloud of points, a shadow, surface geometry, a distance map, or other methods as would be known to one of ordinary skill in the art can be used to represent the initial shape and position of the reference catheter.

Step 203 comprises initiating an algorithm to correct for shift and/or drift of the reference catheter. In one embodiment, the algorithm can comprise the process described in FIG. 2C. In another embodiment, the algorithm can comprise the iterative closest point (ICP) registration method described in FIG. 2D. In yet other embodiments, the algorithm can comprise other processes and methods as described herein. The various algorithms and processes described herein can be used separately, or used together in various combinations.

Step 205 comprises determining a current shape and position of the reference catheter. In one embodiment, a position of a plurality of reference electrodes on the reference catheter can be used to determine the current shape and position of the reference catheter. In another embodiment, the location of the plurality of reference electrodes can be used to create a point cloud of the reference catheter. In yet other embodiments, the methods and processes described herein can be used to determine the current shape and position of the reference catheter. A cloud of points, a shadow, surface geometry, a distance map, or other methods as would be known to one of ordinary skill in the art can be used to represent the current shape and position of the reference catheter. In another embodiment, a distance map can be used to determine a computation efficiency in determining alignment.

Step 209 comprises calculating a closest fit of the current shape and position of the reference catheter to the initial shape and position of the reference catheter. In one embodiment, the system can determine the closest fit by iteratively adjusting a set of registration parameters and evaluating the error of the solution. The error of the solution would be the quality of fit between the registered location of the current catheter position to the original reference shape. The registration parameters used by the algorithm can comprise at least one of translation, rotation, global scale, axis-independent scale, skew, and morphing. The errors from one or more of the registration parameters can generally be a fitness of the current shape and/or position to the original shape and/or position in terms of distance.

Step 211 comprises determining a set of solution parameters. The set of solution parameters can be determined after the closest fit of the current shape and position of the reference catheter to the initial shape and position of the reference catheter has been determined. The set of solution parameters are the changes required to bring the current shape and position of the reference catheter to the best fit position determined by the system.

Figure 2B:
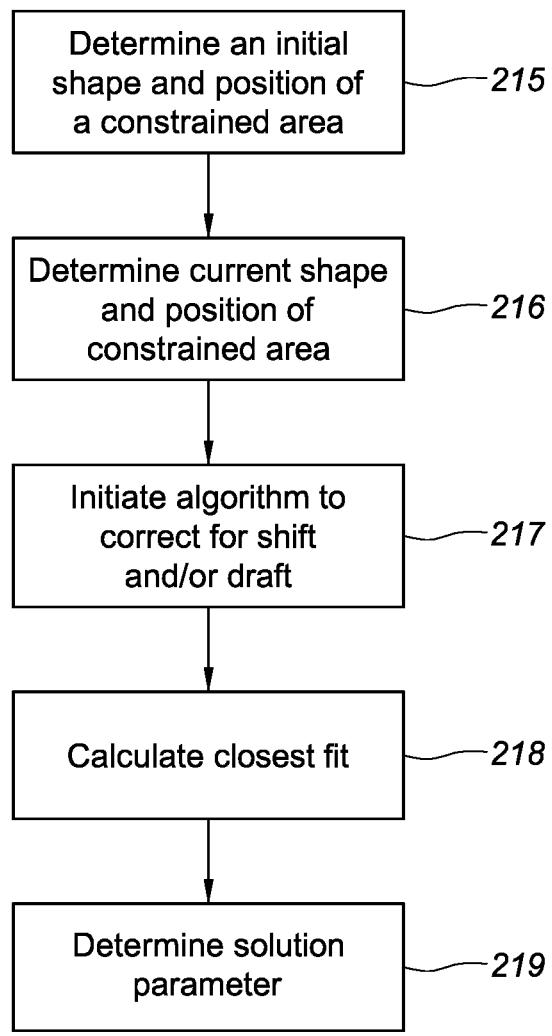
FIG. 2B is a flowchart illustrating one embodiment of a system for determining one or more characteristics of a device

FIG. 2B illustrates a flow chart depicting another embodiment of a system for determining one or more characteristics of a device. The system can comprise an electronic control unit as described in FIG. 1.

Step 215 comprises determining an initial shape and position of a constrained area. In one embodiment, a previously acquired image can be used to determine an initial shape and position of the constrained area. In another embodiment, a position of a plurality of reference electrodes on a catheter can be used to determine an initial shape and position of the constrained area. In yet another embodiment, the location of the plurality of reference electrodes can be used to create a point cloud of the constrained area. In yet other embodiments, the methods and processes described herein can be used to determine the initial shape and position of the reference catheter. A cloud of points, a shadow, surface geometry, a distance map, or other methods as would be known to one of ordinary skill in the art can be used to represent the initial shape and position of the reference catheter. The constrained area can comprise one or more of a pulmonary vein, a plurality of pulmonary veins, an apex of the left ventricle, a superior vena cava, an inferior vena cava, or other constrained areas within the heart or other organs.

Step 216 comprises determining a current shape and position of the constrained area. In one embodiment, a previously acquired image can be used to determine an initial shape and position of the constrained area. In another embodiment, a position of a plurality of reference electrodes on a catheter can be used to determine an initial shape and position of the constrained area. In yet another embodiment, the location of the plurality of reference electrodes can be used to create a point cloud of the constrained area. In yet other embodiments, the methods and processes described herein can be used to determine the initial shape and position of the reference catheter. A cloud of points, a shadow, surface geometry, a distance map, or other methods as would be known to one of ordinary skill in the art can be used to represent the initial shape and position of the reference catheter. The constrained area can comprise one or more of a pulmonary vein, a plurality of pulmonary veins, an apex of the left ventricle, a superior vena cava, an inferior vena cava, or other constrained areas within the heart or other organs. By determining a current shape and position of the constrained area through a point cloud, or other method, the current shape and position of the constrained area can be compared to a previous shape and position of the constrained area. Further, if using a plurality of constrained areas, i.e. a plurality of pulmonary veins, a pulmonary vein and an apex of the left ventricle, etc, less degrees of freedom are present for the model to determine. If the degrees of freedom are limited enough through a plurality of constrained areas, it is possible that there would be only one way that the current shape and position of the constrained area can fit into the initial shape and position. In another embodiment, the shape and position of the constrained area can be used with a reference catheter as described herein to the best fit position determined by the system.

Step 217 comprises initiating an algorithm to correct for shift and/or drift of the reference catheter. In one embodiment, the algorithm can comprise the process described in FIG. 2C. In another embodiment, the algorithm can comprise the iterative closest point (ICP) registration method described in FIG. 2D. In yet other embodiments, the algorithm can comprise other processes and methods as described herein. The various algorithms and processes described herein can be used separately, or used together in various combinations. In one embodiment, Step 217 can be performed when a physician or other user determines that shift and/or drift may have occurred. In other embodiments, a reference catheter can be kept within the constrained area and Step 217 can occur automatically as discussed in other embodiments herein. When using the system for determining one or more characteristics of a device described in FIG. 2B, the current shape and position of the constrained area need to exist in the initial shape and position of the constrained area. The area of the initial shape and position of the constrained area needs to be at least as great as the points collected in the current shape and position of the constrained area. In one embodiment, if extraneous points are collected in the current shape and position, the additional points can be trimmed or otherwise removed from the collection of locations in the current shape and position. In one embodiment, a physician can manually remove the additional points.

Step 218 comprises calculating a closest fit of the current shape and position of the constrained area to the initial shape and position of the constrained area. In one embodiment, the system can determine the closest fit by iteratively adjusting a set of registration parameters and evaluating the error of the solution. The error of the solution would be the quality of fit between the registered location of the current constrained area position to the original constrained area shape. The registration parameters used by the algorithm can comprise at least one of translation, rotation, global scale, axis-independent scale, skew, and morphing. The errors from one or more of the registration parameters can generally be a fitness of the current shape and/or position to the original shape and/or position in terms of distance.

Step 219 comprises determining a set of solution parameters. The set of solution parameters can be determined after the closest fit of the current shape and position of the constrained area to the initial shape and position of the constrained area has been determined. The set of solution parameters are the changes required to bring the current shape and position of the constrained area to the best fit position determined by the system.

Figure 2C:
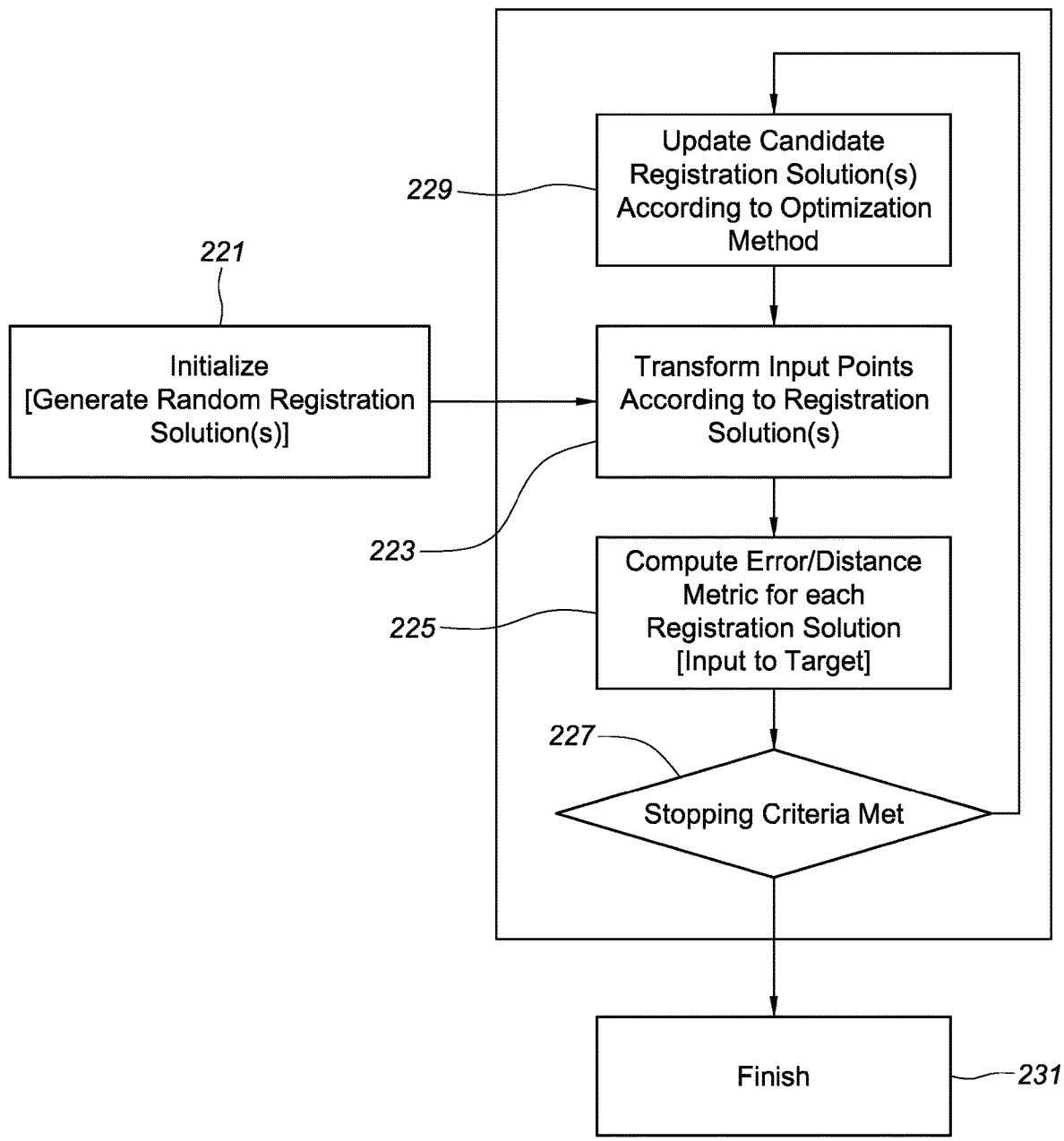
FIG. 2C is a flowchart illustrating a re-registration process.

FIG. 2C illustrates a flow chart depicting one embodiment of a method used by a system using a generalized re-registration method for an electric field based positioning system as described herein. The system can enter into the re-registration process at a time defined by the system. The system can then perform the steps in the re-registration process to determine whether the determined position of the reference catheter has changed from the previously determined location. If the determined position has changed, the re-registration process can be iterated until a stopping criteria has been met. Step 221 comprises the systems entry into the re-registration process. The system can initialize the process and generate at least one random registration solution. Entry into the re-registration process can be determined in several different ways by the system. In one embodiment, entry into the re-registration process can occur when the system determines that the input point cloud has moved a defined distance from the target. The defined distance can be preset within the system, or the defined distance can be chosen by a user of the system before or during a procedure. In another embodiment, entry into the re-registration process can occur at times chosen by a user of the system. In one embodiment, a display or other device can comprise a button or other method to signal to the system to start the re-registration process. In yet another embodiment, entry into the re-registration process can occur after a defined length of time since the last re-registration process started. The defined length of time can be preset into the system, or the defined length of time can be chosen by a user of the system before or during a procedure. In yet another embodiment, entry into the re-registration process can occur after a defined length of time since the last registration process ended. The defined length of time can be preset into the system, or the defined length of time can be chosen by a user of the system before or during a procedure. In a preferred embodiment the re-registration algorithm would be run continuously from the inception of the setting the reference catheter as the target.

Step 223 comprises transforming the input points according to the at least one registration solution determined in step 221.

Step 225 comprises computing an error and/or distance metric for each of the at least one registration solution.

Step 227 comprises determining whether the stopping criteria has been met. There are several different mechanisms that can be used for determining the stopping criteria for the method described herein. One example mechanism to determine if the stopping criteria has been met can comprise reaching a computed error less than a threshold error. The threshold error can be preset with the system, or chosen by a user of the system. A second example mechanism to determine if the stopping criteria has been met can comprise determining whether a number of max iterations of the method or process described herein have been performed. The number of max iterations can be preset with the system, or chosen by a user of the system. If the stopping criteria has been met, the method proceeds to step 231 and the system exits the re-registration process. If the stopping criteria has not been met, the method proceeds to step 229. In a preferred embodiment where the algorithm is being run continuously, the re-registration algorithm would not stop and would continuously attempt to adapt the input point cloud which is the current state/position of the reference catheter to the original reference target.

Step 229 comprises updating the at least one registration solution according to the optimization method used during the re-registration process. One or more optimization methods can be used during this step. The optimization methods can comprise a gradient descent method, a conjugate gradient method, a stochastic gradient descent, Newton's method, a quasi-Newton method, a particle swarm optimization method, an ant colony optimization method, an artificial bee colony algorithm, a simulated annealing method, a Levenberg-Marquardt algorithm, or other optimization methods as would be known to one of ordinary skill in the art. The method then moves again to step 223 transforms the input points according to the at least one registration solution determined in step 221. As stated above in relation to step 227, the system continues performing the method described herein until the stopping criteria is met, and the re-registration process exits. The system can then restart the method as described above in relation to step 221.

Figure 2D:
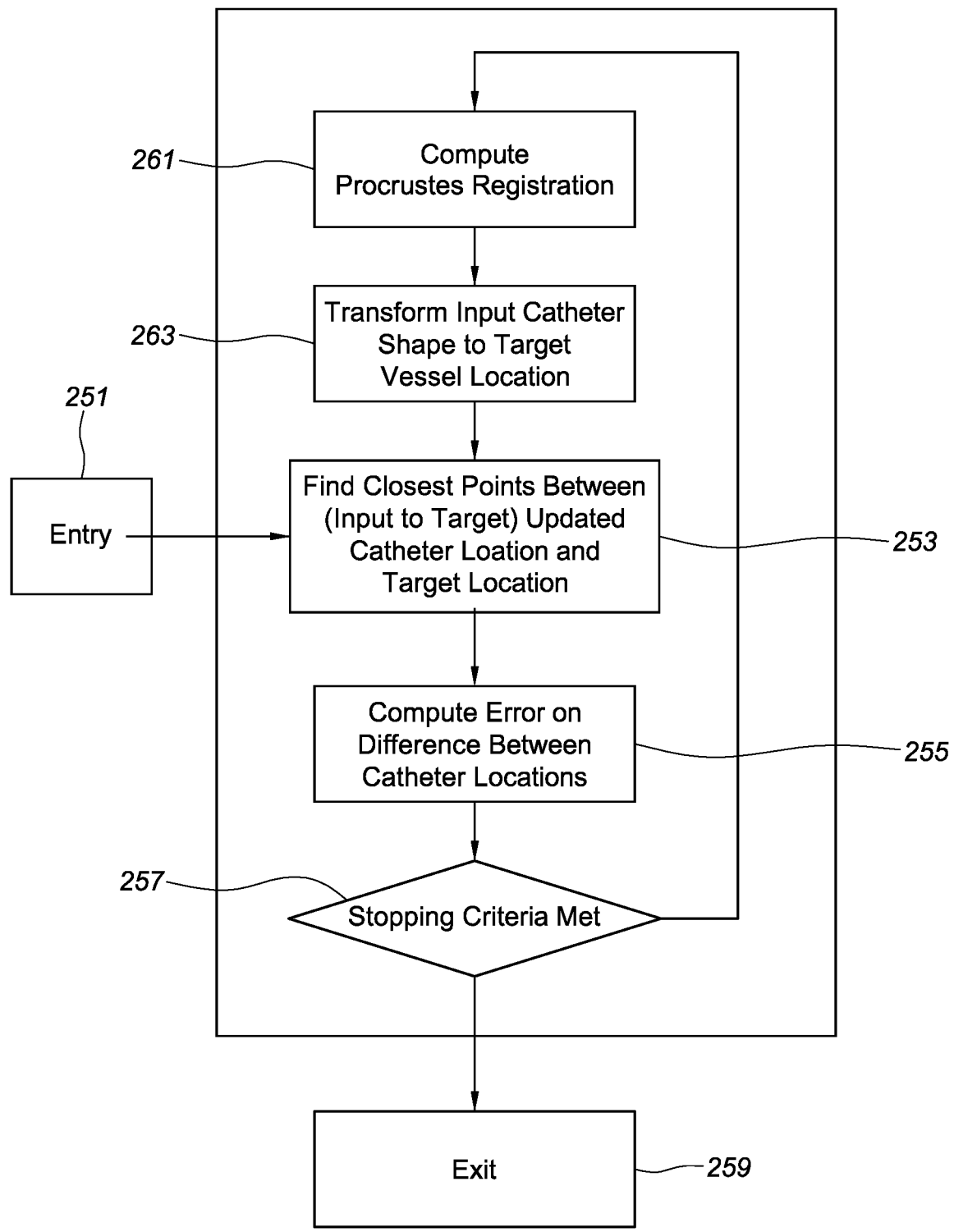
FIG. 2D is a flowchart illustrating an iterative closest point registration process.

FIG. 2D illustrates a flowchart depicting another embodiment of a method used by a system to correct for positional errors as discussed herein. The method illustrated in FIG. 2D comprises an ICP registration method. Step 251 comprises the systems entry into the ICP registration process. As stated above in relation to FIG. 2C, entry into the ICP registration process can be determined in several different ways by the system.

Figure 3:
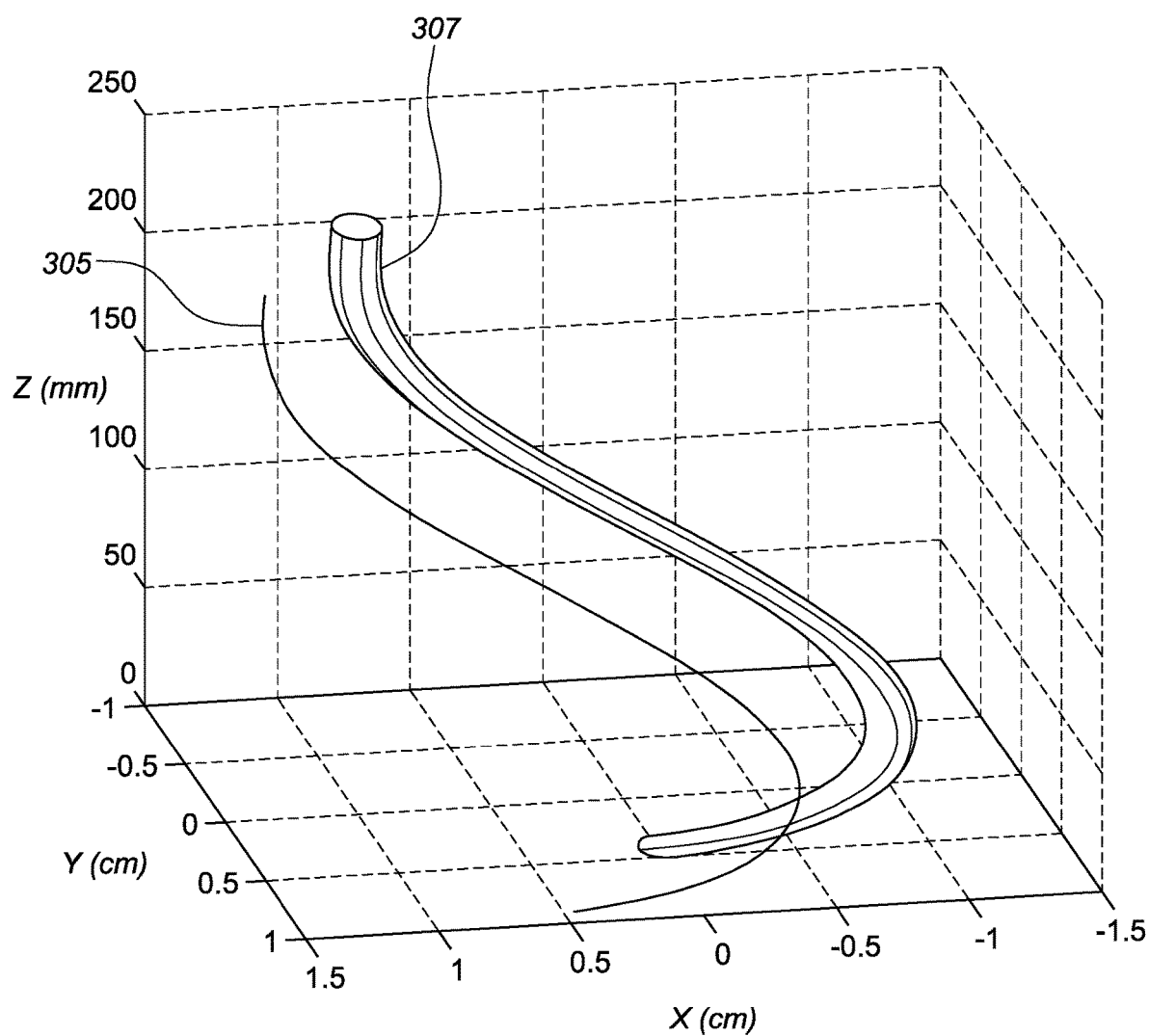
FIG. 3 is a view of a model undergoing an interactive closest point registration process.

Step 253 comprises finding the closest points between the target and the input point cloud. These closest points being referred to as fiducial point pairs. A representation of the target and input point cloud is illustrated in FIG. 3.

Step 255 comprises computing an error between the target and the input point cloud. The method to compute the error can comprise a Euclidean norm error as described. Further, the method can comprise using an RMS error. The Euclidean norm is considered to be the L2 norm. Another method to compute the error can comprise the L1 norm. The L1 norm can be the absolute value of the difference between the x, y, and z coordinates. Further, any L-infinity norm can also be used as it would tend to minimize the maximum distance of any of the fiducial point pairs. The Euclidean Norm can be determined by the following equation. The error 'e' is the Euclidean norm of the vector offsets between the input locations and the target locations.

$$\|e\|_2 = \left(\sum_{n=1}^{N} |x_n - y_n|^2\right)^{\frac{1}{2}}$$

Further, the L-p Norm can be determined by the following equation. The error 'e' is the L-p norm of the vector offsets between the input locations and the target locations $$\|e\|_p = \left(\sum_{n=1}^{N} |x_n - y_n|^p\right)^{\frac{1}{p}}$$

Step 257 comprises determining whether the stopping criteria has been met. There are several different mechanisms that can be used for determining the stopping criteria for the method described herein. Some of the mechanisms used for the stopping criteria are described above in FIG. 2C. If the stopping criteria has been met, the method proceeds to step 259 and the system exits the ICP registration process. If the stopping criteria has not been met, the method proceeds to step 261. In a preferred embodiment where the algorithm is being run continuously, the ICP registration algorithm would not stop and would continuously attempt to adapt the input point cloud which is the current state/position of the reference catheter to the original reference target.

Step 261 comprises computing a Procrustes registration algorithm. A Procrustes registration algorithm can be used to overlay the data points if a point correspondence between the two images or point clouds is known between the target reference catheter and the input reference catheter. Procrustes registration comprises using the fiducial point pairs determined in step 253 to align the input point cloud to the target using the homogeneous transformation determined by the algorithm. Step 263 comprises transforming the input points. The input points can be transformed in view of the Procrustes registration performed in step 261. The method then moves again to step 253 and finds the closest points between the input point cloud and the target. As stated above in relation to step 257, the system continues performing the method described herein until the stopping criteria is met, and the ICP registration process exits. The system can then restart the method as described above in relation to step 251.

One procedure that can be used to correct errors of shift and/or drift comprises point based registration. In one embodiment, point based registration can comprise iterative closest point (ICP) registration. FIG. 3 illustrates a model undergoing an interactive closest point registration process. An iterative closest point registration process comprises comparing two point clouds (or a point cloud and a target object defined by geometrical information other than by points) that have no previously registered or otherwise known point correspondence. The ICP registration method comprises a target 307, and an input point cloud 305. In some embodiments, the target 307 can comprise a target point cloud. The target can comprise one of a point cloud, a shadow, and/or a geometry. To align the target 307 and the input point cloud 305, the procedure can be initialized by defining the target geometry as the coronary sinus or other vessel geometry, for example. The target geometry may be determined based on sensed or otherwise determined locations of any electrodes present on the reference catheter by means of the navigation and localization system. Moreover, supplemental sample points may be made by sampling a spline that was computed or otherwise determined by the sensed location of a plurality of electrodes present on the reference catheter. The coronary sinus or other vessel can be represented as a point cloud, as a closest point distance transform, or through another mechanism as would be known to one of ordinary skill in the art.

Figure 4:
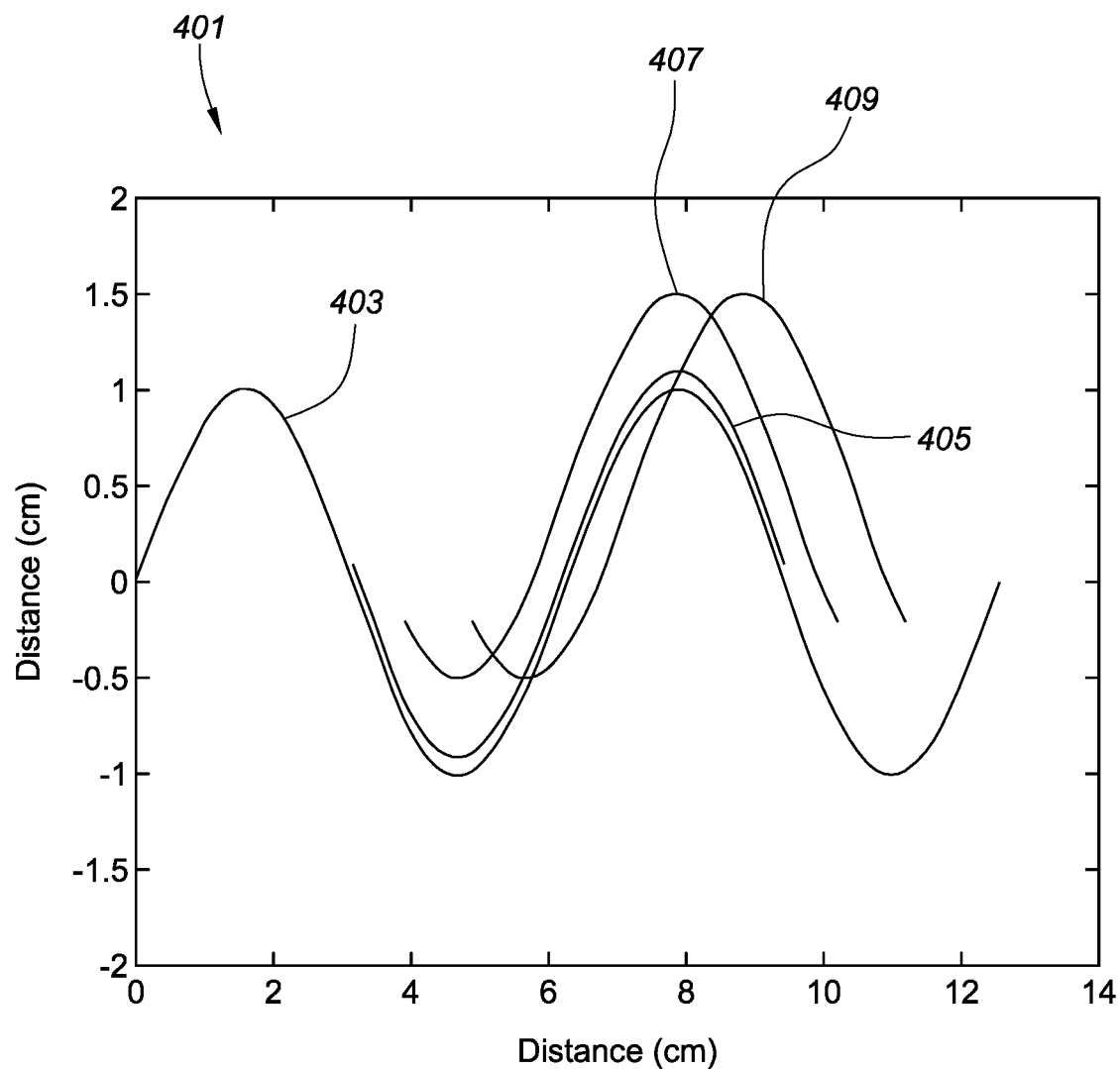
FIG. 4 is a display showing several versions of a reference catheter that have undergone various forms of shift/drift and/or dislodgement represented as 2D for simplicity.

FIG. 4 is a display 401 illustrating several versions of a reference catheter that has undergone various forms of error as discussed herein. The display 401 illustrates a determined representation of the coronary sinus 403, a detected location of the reference catheter at time 0 405 as discussed above, a Y-axis shift reference catheter 407 that comprises a detected location of the reference catheter after a Y-axis shift, and a XY-axis shift reference catheter 409 that comprises a detected location of the reference catheter after an XY-axis shift. The detected location of the reference catheter at time 0 405, the Y-axis shift reference catheter 407, and the XY-axis shift reference catheter 409 are all illustrated in relation to the determined representation of the coronary sinus 403. A reference catheter can be seen secured within the coronary sinus in FIG. 1. FIG. 1 illustrates a plurality of reference electrodes 43 on a reference catheter 41 disposed within the coronary sinus. The determined representation of the coronary sinus 403 can be determined through methods and processes such as those described in FIG. 9. In other embodiments, the determined representation can comprise a different vessel. Returning to FIG. 4, the reference catheter 405 is illustrated after it has become dislodged, but without having experienced any shift/drift. The Y-axis shift reference catheter 407 illustrates the detected location of the reference catheter 405 after the dislodged reference catheter has experienced a shift and/or drift in the Y-axis. They XY-axis shift reference catheter 409 illustrates the detected location of the reference catheter 405 after the dislodged reference catheter has experienced a shift and/or drift in the X-axis and the Y-axis. A detected location as that illustrated by the reference catheter 405 can be used to determine whether the detected reference catheter has possibly undergone a dislodgement from the coronary sinus or other vessel where the reference catheter was previously anchored. One advantage of using an ICP registration process is that each of the point sets or point clouds does not need to be complete. This can be important as in some circumstances, the reference catheter can only span a portion of the geometry of the coronary sinus or other vessels. A target geometry may be defined by sampling a greater extent of the vessel than the reference catheter electrodes may possibly span. One method by which this can be accomplished is to collect a cloud of points while moving the catheter distally and proximally within the vessels. The target geometry can be defined as the raw set of points collected. Alternatively it can be represented as a closest point distance transform, a surface geometry or through another mechanism as would be known to one of ordinary skill in the art.

Another procedure that can be used to correct errors of shift and/or drift comprises point correspondence. Point correspondence refers to taking two or more three dimensional (3D) models and finding a set of points in one model which can be identified as the same points in a second model. There are several ways that this process can be accomplished. First, a set of points from a first model can be correlated to a set of points from a second model. A second way that the process can be accomplished is finding a feature in the set of points from a first model and determining whether that feature is similarly shown in the second model. When creating a set of models of the reference catheter to compare using point correspondence several factors need to be taking into consideration. First, a model of the target reference catheter, the position and shape of the reference catheter taken at time 0 or otherwise used as a reference for the method or system, can comprise a plurality of points or a volume. A volume can comprise a plurality of geo points, a shadow, or a geometry. Second a model of the input reference catheter, the position and shape of the reference catheter taken at time t or as detected in real time, can comprise a plurality of points. The plurality of points can comprise any electrodes present on the reference catheter or a super sampled spline created by a system that can be created using known information about the reference catheter. The super sampled spline can be created from detected electrode locations on the reference catheter. In one embodiment, the system can further use known information relating to the location of the various electrodes on the reference catheter to further determine the shape of the super sampled spline.

Figure 5A:
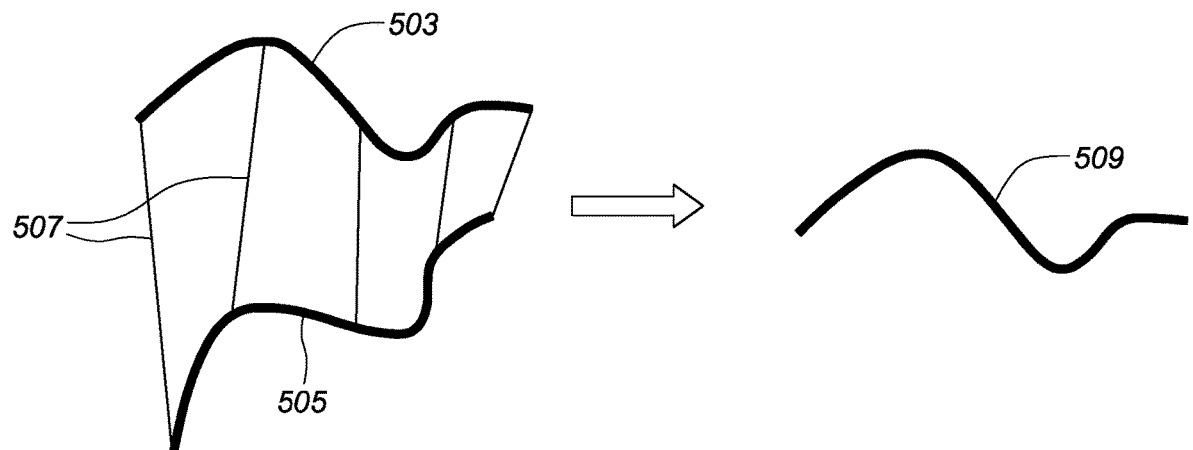
FIGS. 5A and 5B are side views of reference catheters that have undergone shift/drift and the resulting correction using point correspondence.
Figure 5B:
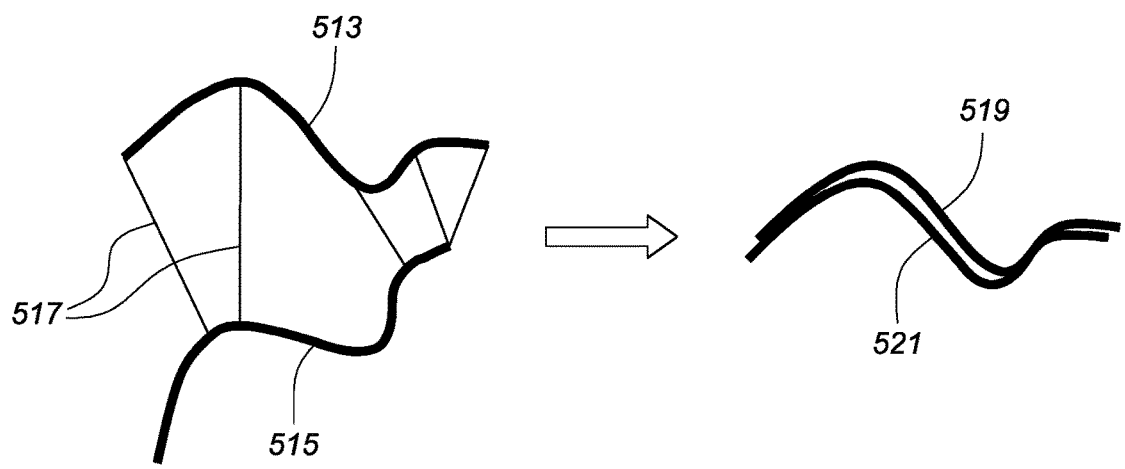

FIGS. 5A and 5B illustrate the different results that are achieved from correcting for shift and/or drift when point correspondence between the plurality of images is known and when the point correspondence between the plurality of images is unknown. FIG. 5A illustrates an embodiment where the point correspondence is known. FIG. 5A comprises a target reference catheter location 503, an input reference catheter location 505, a plurality of point correspondence lines 507, and a combined reference catheter location 509. The target reference catheter location 503 is the position and shape of the reference catheter taken at time 0 or otherwise used as a reference for the method or system. The input reference catheter location 505 is the position and shape of the reference catheter taken at time t or as detected in real time. The plurality of point correspondence lines 507 illustrate the connection points between the target reference catheter location 503 and the input reference catheter location 505. Each of these lines connect corresponding locations on each of the reference catheter locations. The combined reference catheter location 509 is a merged or composite image of the target reference catheter location 503 and the input reference catheter location 505.

FIG. 5B illustrates an embodiment where the point correspondence is not known. In one embodiment, the point correspondence can be determined iteratively. FIG. 5B comprises an initial target reference catheter location 513, an initial input reference catheter location 515, a plurality of point correspondence lines 517, a final target reference catheter location 519, and a final input reference catheter location 521. The initial target reference catheter location 513 is the position and shape of the reference catheter taken at time 0 or otherwise used as a reference for the method or system. The initial input reference catheter location 515 is the position and shape of the reference catheter taken at time t or as detected in real time. The plurality of point correspondence lines 517 illustrate the system's attempts to find connection points between the initial target reference catheter location 513 and the initial input reference catheter location 515. Each of these lines connect to points that may be corresponding locations on each of the reference catheter locations. As seen in FIG. 5B, the plurality of point correspondence lines 517 are not as accurate as those seen in FIG. 5A. As a result, after the point correspondence process has been completed, the final target reference catheter location 519 and the final input reference catheter location 521 are not an exact match. Instead, as a result of the misplacement of the plurality of point correspondence lines 517, the final target reference catheter location 519 and the final input reference catheter location 521 are instead close to each other, but not completely overlapping. In one embodiment, as shown above in FIG. 3, the process can be repeated until a set number of iterations has been run, or a distance between the two images is less than a threshold distance. However, the iterative correspondence and registration process can often achieve a registration accuracy as accurate as when the exact correspondence is known apriori.

As shown in FIG. 5A and discussed in FIG. 2D, if a point correspondence is known between the target reference catheter and the input reference catheter, the registration of the two images or point clouds can be achieved without extra steps. By known the point correspondence between the two images or point clouds a Procrustes registration and/or a thin-plate splines registration can be used to overlay the data points. However, as illustrated in FIG. 5B, if a point correspondence is not known between the target reference catheter and the input reference catheter, the registration of the two images or point clouds can be more difficult, and more work can be necessary to properly overlay the acquired data. In general, the scenario shown in FIG. 5B is the scenario that will exist in practice. Due to the potential for dislodgement and general lack of additional a-priori information to determine the exact correspondence of matching point between the input point cloud and target, another method must be used to determine the correspondence. In this instance, a point matching algorithm as described herein can be used. Several different embodiments of a point matching algorithm can be used to achieve the desired results.

In one embodiment, a process that can be used for the point matching algorithm comprises a standard closest point method. The closest point method comprises comparing the distance between the points of the two images or point clouds and continuing to iterate the process as described above. However, the closest point method can be a slow, resource intensive process. In a second embodiment, a process that can be used for the point matching algorithm comprises a normal shooting method. The normal shooting method comprises taking every point in an input cloud of points and computing the distance between each point (the normal point) and X number of nearest points in the target cloud. The X number of points can be preset within the system, or otherwise chosen by a user before or during a procedure. Among the X number of points, the point that has the least distance to the normal point is considered as the corresponding point in the target cloud. In one embodiment, after every point in the input point cloud has been run through the normal shooting method, a total distance between the plurality of points present in the input point cloud and the target can then be determined. If the total distance is below a threshold total distance, then the process can stop. If the threshold distance is above the threshold, the process can repeat. However, one disadvantage of this process is that it can be system intensive or otherwise perform poorly when attempting to correspond a noisy representation of the target or input. The third process that can be used for the point matching algorithm comprises considering only compatible points. In a generalized ICP algorithm, compatible points can be determined by looking for the same or similar local features including curvature of the image or cloud of points, the same or similar normals, the same or similar colors, etc. In one embodiment, where an electro-anatomical imaging system is used, compatible points can further be determined by using electrode spacing on the reference catheter. Electrode spacing is an indication of local impedance field non-uniformity which can be used as a unique feature to determine the correspondence of the input to the target where this same electrode spacing was recorded at time zero. In yet another embodiment, where an electro-anatomical imaging system is used, a sensor or other identifiable portion of the reference catheter can be used to determine compatible points. In a mode where the ICP algorithm is being continuously updated, the point correspondence may be easier (or become easier after convergence is achieved through multiple iterations). When the input and target are closely aligned determining the correspondence can be achieve through a search with limited range as can be appreciated from 519 and 521 in FIG. 5B.

In addition to the above methods and processes relating to point correspondence, additional mechanisms can be used to further accelerate the speed that the process can be run. These methods include using K-d Trees, using a closest point distance transform, and using different Graphical Processing Units (GPU's), among other methods. K-d Trees comprise searching a space iteratively that has been subdivided in half along a particular axis. When considering a point within a box formed by the subdivision, it is not necessary to search all candidates within every box. The box that contains that candidate point is searched first, followed iteratively by the next layer of adjacent boxes. Once a closest point is found it is not necessary to search further adjacent boxes because they cannot contain a point that is any closer. This process can significantly speed up the algorithm used for closest point search. Further, a closest point distance transform (CPDT) can comprise making an organized grid that encompasses the plurality of points, and determining a distance and a vector to the next closest point. A CPDT can be obtained by growing surfaces in layers from the boundary of the target. While a CPDT can be relatively expensive in terms of system resources and time to learn up front, the information gathered from the closest point distance transform can be very efficient for the system to recall at a future point in time. Once the CPDT is learned, determining the closet point can become a single look-up step. By using a GPU with multiple cores, or other process and hardware configured to speed up the processing of information necessary to run a point correspondence, multiple point distances can be computed in parallel within the GPU. However, sorting on the GPU can still be relatively system and time intensive.

As the degrees of freedom present within a system expand, the difficulty of determining accurate results that satisfy every included degree of freedom (DOF) increases. A standard iterative closest point registration process can account for 6 degrees of freedom, 3 DOF can be present with translation of the reference catheter, and 3 DOF can be present with rotation of the reference catheter. Combined, translation and rotation can account for 6 DOF. However, higher degree changes may be an additional source of error and in some embodiments of the disclosure, 7 to 9 DOF corrections may be desirable.

One method of obtaining results that can include more degrees of freedom than those present from an iterative closest point registration is to process the plurality of points with particle swarm optimization. Particle swarm optimization is a computational process that can optimize a problem by iteratively trying to improve a candidate solution with regard to a given measure of quality, referred to as an objective function. Particle swarm optimization solves a problem by having a population of candidate solutions, here dubbed particles, and moving these particles around in the search-space according to simple mathematical formulae over the particle's position and velocity. Each particle's movement is influenced by its local best known position but, is also guided toward the best known positions in the search-space, which are updated as better positions are found by other particles. This is expected to move the swarm toward the best solution. In some embodiments, the particle can be an N-D particle. In one embodiment, the N-D particle can comprise the following coordinates, [tx, ty, tz, rx, ry, rz, s]. In another embodiment, the N-D particle can comprise the following coordinates, [tx, ty, tz, rx, ry, rz, sx, sy, sz]. In the above coordinates, the "t" of x, y, and z comprise a reference to translation. Further, in the above coordinates, the "r" of x, y, and z comprises a reference to rotation.

Figure 6:
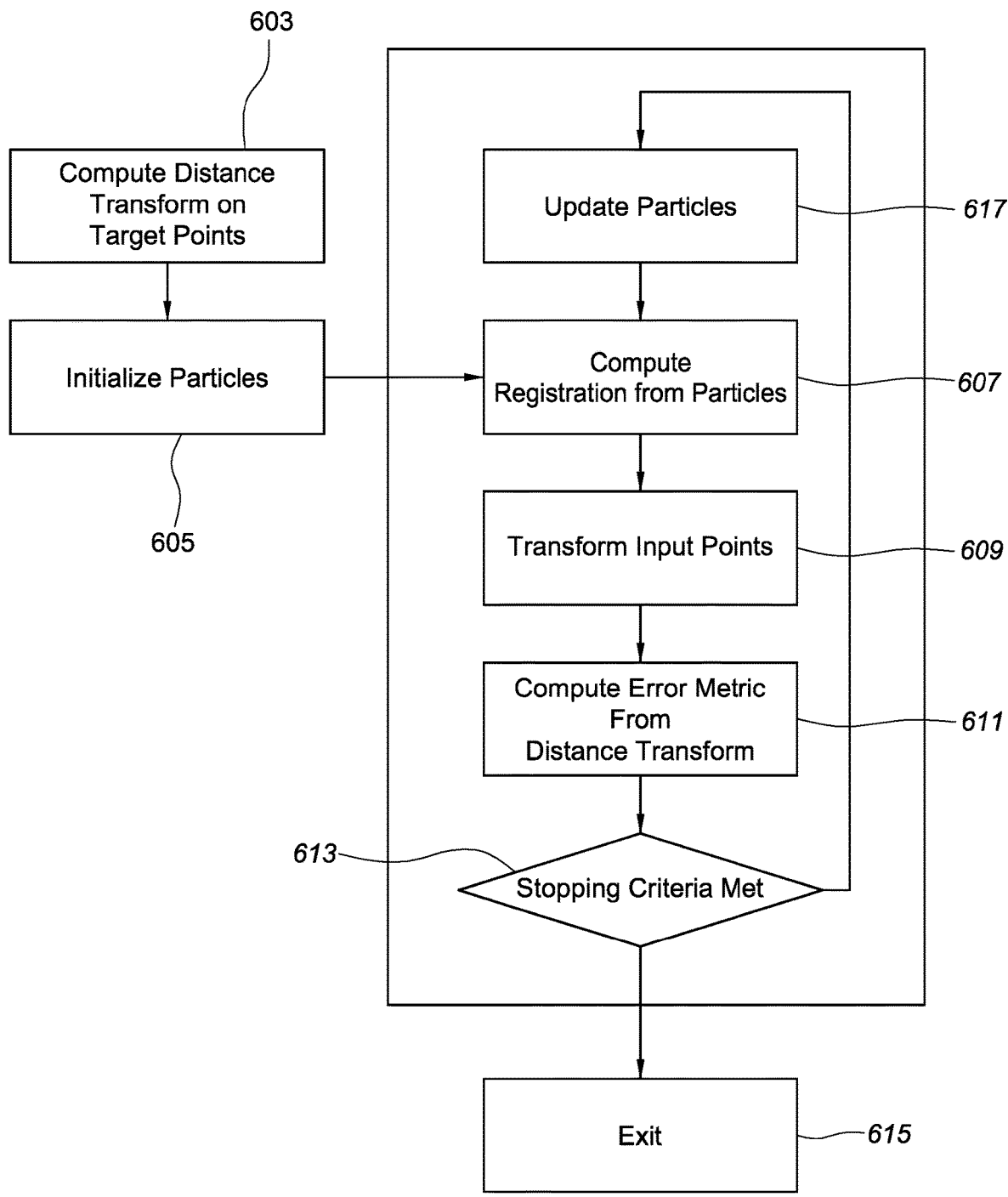
FIG. 6 is a flowchart illustrating an embodiment of a swarm optimization process that comprises an iterative point based method.

FIG. 6 illustrates a particle swarm optimization process that can be used as an alternative to an iterative closest point method for determining an optimal registration. As previously mentioned each particle defines a potential solution to the registration transformation. Particles are evaluated and updated according to the outline method until the algorithm converges to an optimal solution. Step 603 comprises computing a distance transform on target points within the point cloud. Step 605 comprises initializing the particles. Step 607 comprises computing a registration from the particles. Step 609 comprises transforming the input points. Step 611 comprises computing an error metric from the distance transform. Step 613 comprises determining whether the stopping criteria has been met. If the stopping criteria has been met, then proceed to step 615 and exit the particle swarm optimization process. Also, as mentioned previously with the iterative closest point method, the algorithm can be defined to run continuously and not stop in order to continuous track shifts/drifts or artifact motion. If the stopping criteria has not been met, then proceed to step 617 and update the particles. Then continue to step 607 and repeat the process described herein. One advantage of this method is that only a distance transform can be required, and in some embodiments, no closest point transform is required. Further, correspondence is not needed, instead only an error metric is required, which is the objective function. The particle swarm optimization process described herein does not require computation of a gradient which is typically required for other optimization techniques. This is more efficient, though it does require many particles which will need to be evaluated by the process.

Figure 7:
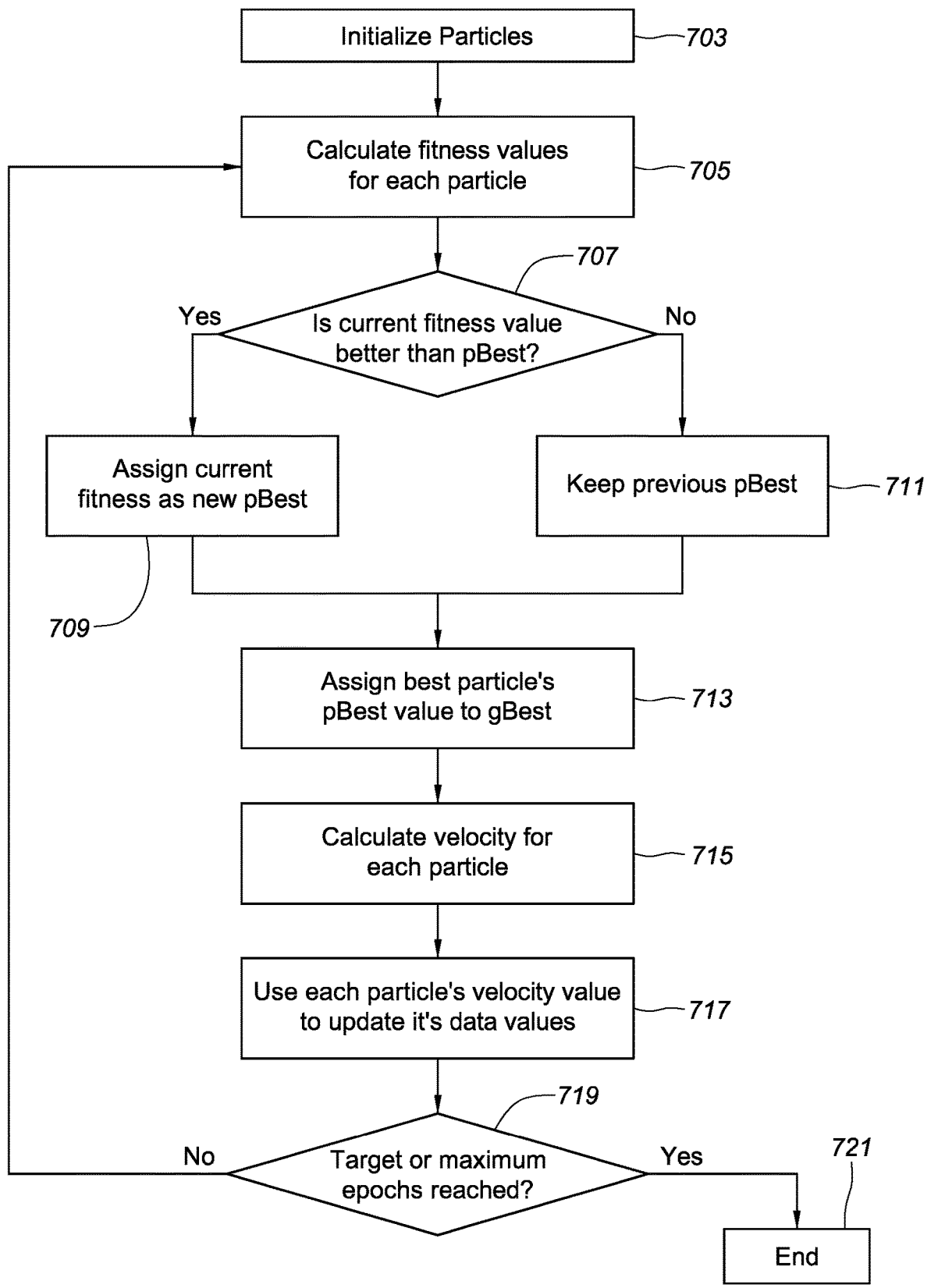
FIG. 7 is a flowchart illustrating another embodiment of a swarm optimization process that comprises a method of evolutionary computing.

FIG. 7 illustrates a more detailed description of the generalized particle swarm optimization process, which can be thought of as evolutionary computing based on social behaviors. Social behaviors can be modeled on the movement of objects found in nature such as the flight patterns of a flock of birds or the swimming patterns of a school of fish. Step 703 comprises initializing the plurality of particles. Step 705 comprises calculating a fitness value for each of the plurality of particles, which is the objective function which is being minimized. Step 707 comprises determining whether the fitness value for each of the plurality of particles is better than pBest (the particle coordinates for this particle that has the best fitness from all previous iterations). If the answer to step 707 is yes, the fitness value for that particular particle is better than pBest, then proceed to step 709 and assign the current fitness value as the new pBest. If the answer to step 707 is no, the fitness value for that particular particle is not better than pBest, then proceed to step 711 and keep the previous pBest. After either step 709 or step 711, proceed to step 713 and assign the best particles pBest value to gBest (the particle coordinates from the entire set of particles that has the best fitness from all previous iterations). Step 715 comprises calculating a velocity for each of the plurality of particles. Step 717 comprises using each of the plurality of particle's velocity value to update that particles data values. Step 719 comprises determining whether a target or maximum number of epochs have been reached. If the target or maximum number of epochs have not been reached, then proceed to step 705 and start the iterative process again by calculating a fitness value for each of the plurality of particles. If the target or maximum number of epochs has been reached, then proceed to step 721 and end the particle swarm optimization process. The method shown in FIG. 7 can review particles that are candidate solutions to optimization problems in the N-D particles discussed above. The particle swarm optimization process of FIG. 7 is well suited to avoid local minima, which is a challenge amongst other optimization methods. The process relies only on a computation of "fitness" for each of the plurality of particles. Further, the process described herein does not require a computation of a gradient or a Jacobian. In other embodiments, other optimization methods may be used. Other optimization methods can comprise Levenberg-Marquardt, gradient descent, simulated annealing, and others that would be known to one of ordinary skill in the art.

Several other options are also possible to optimize the processes described herein. First, a coherent point drift algorithm can be used. Second an iterative closest point registration can be used that further comprises using a thin plate spline method as described above instead of a Procrustes registration. When using a thin plate spline process with an iterative closest point registration, the lambda, or stiffness parameter, of the thin plate spline can be started at a high value. Further, the lambda, or stiffness parameter, can be slowly decreased as the iterative process is ran to achieve a desired error metric. In some embodiments, a Thin Plate Splines algorithm (which incorporates Procrustes) can be allowed to converge until it reaches a minimum. In one embodiment, if the error metric is above a threshold, the lambda/stiffness parameter can be reduced and allowed to converge again. This process can continue until the error metric is attained or a minimum lambda is reached.

There are several different implementation procedures that can be used for the processes and methods described herein. The first implementation procedure is a slow update. The slow update comprises a slow, iterative update. When using the slow update method, a background stable filter can be used. By using a slow update, a homogeneous transformation matrix can be added to the visualization and mapping system filter chain. However, the slow update process will not instantly compensate for a sudden shift, as the stable filter can introduce lag. The second implementation procedure is a fast update. The fast update comprises a continuous updating transform and can require respiration and cardiac binning. This information can act as respiration and cardiac compensation and in some embodiments can replace the coronary sinus or other vessel reference. For both implementation procedures the optimization process does not have to start from the original catheter location. Instead, the optimization process can start from the previous location of the last re-registration. The ability to start from the previous best solution will minimize the computational burden as the initial solution may already be relatively close to the optimal solution.

Figure 8A:
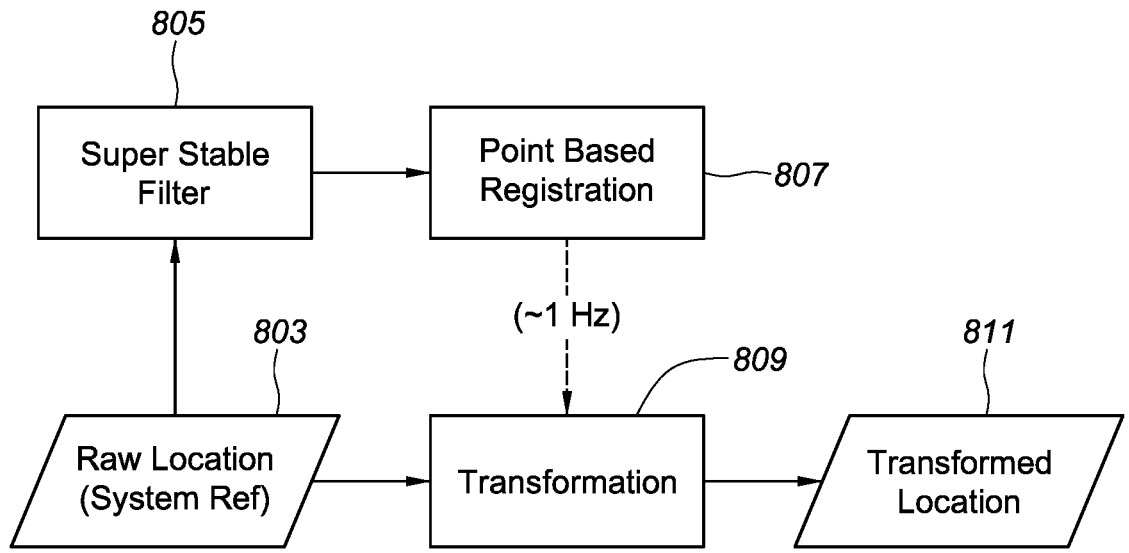
FIGS. 8A and 8B are flowcharts illustrating a slow and fast update implementation procedure.

FIG. 8A illustrates the slow update implementation procedure. Step 803 comprises a raw location or system reference. Step 805 comprises passing the raw location or system reference through a super stable filter. Step 807 comprises performing a point based registration on the filtered raw location or system reference. Step 809 comprises running a transformation on the filtered raw location or system reference. In one embodiment, this can occur at around 1 Hertz. Step 811 comprises determining the transformed location and outputting the transformed location to a system or other device. In the slow update embodiment, the re-registration method is attempting to compensate for only the shift/drift component or the "DC" component of the error.

Figure 8B:
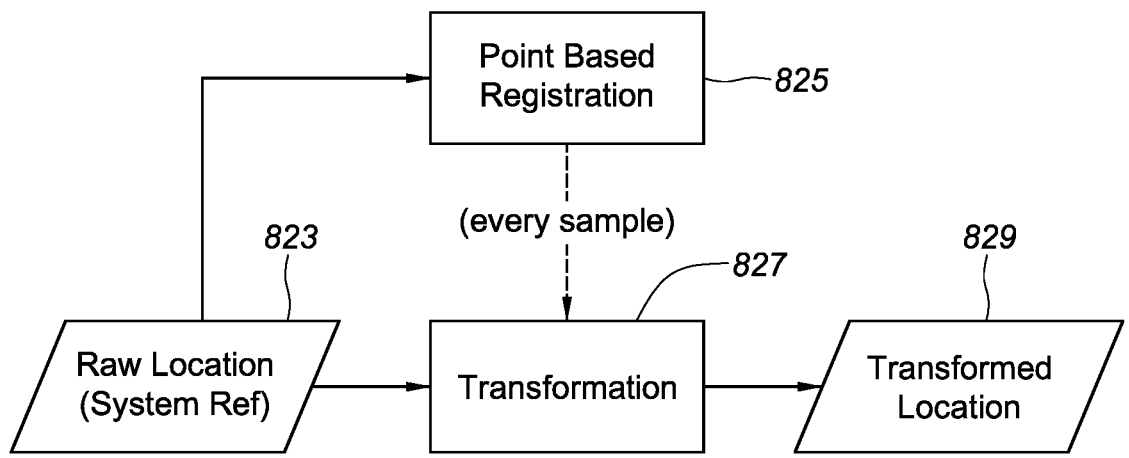

FIG. 8B illustrates a fast update implementation procedure. Step 823 comprises a raw location or system reference. Step 825 comprises performing a point based registration on the raw location or system reference. Step 827 comprises running a transformation on the raw location or system reference. In one embodiment, this can occur to every sample. Step 829 comprises determining the transformed location and outputting the transformed location to a system or other device. In the fast update embodiment, the re-registration method is attempting to compensate for the shift/drift component as well as other effects such as cardiac or respiratory artifacts.

The methods and systems described herein can be further extended to other domains. In one embodiment, the methods and systems can be used to register the coronary sinus or other vessel within a heart or other portion of the vasculature system. In one embodiment, a majority of the coronary sinus or other vessel can be registered. In another embodiment, a portion of the coronary sinus or other vessel can be registered. By registering the coronary sinus or other vessel, the location and configuration of the vessel can be determined and used during a procedure. The registered vessel can be further utilized during the procedure to assist with lead implantation, electroanatomical mapping, image fusion, and image integration. Further by registering the vessel explicit identification of fiducial points are not required.

Figure 9:
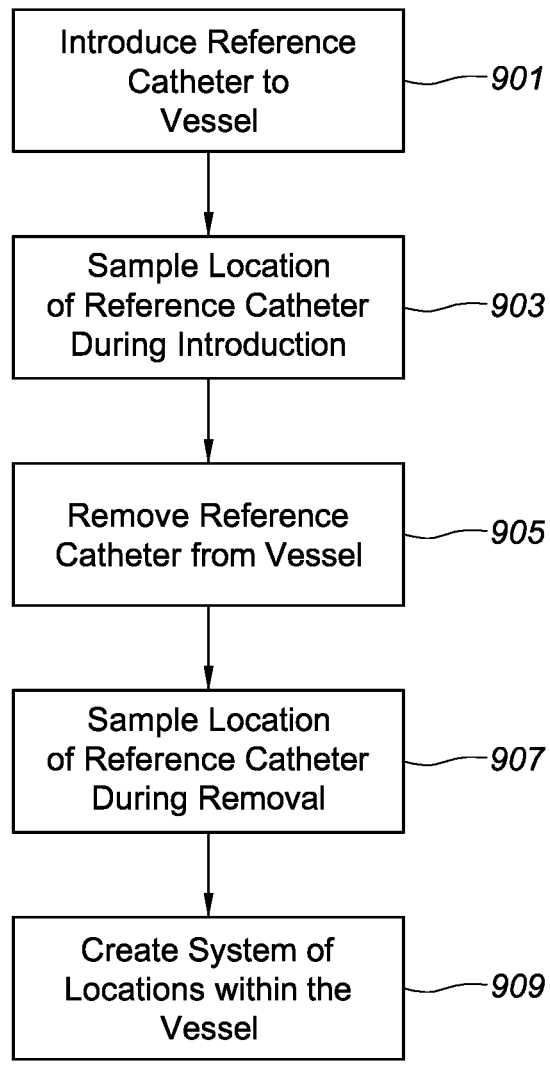
FIG. 9 is a flowchart illustrating a process to create a geometry of a coronary sinus or other vessel.

FIG. 9 illustrates a flow chart to create a geometry of the coronary sinus or other vessel as reference catheter is introduced to the vessel. Step 901 comprises introducing the reference catheter slowly into the vessel. Step 903 comprises sampling the location of a plurality of electrodes on the reference catheter while the reference catheter is being introduced into the vessel. Step 905 comprises slowly removing the reference catheter from the vessel. Step 907 comprises sampling the location of the plurality of electrodes on the reference catheter. Step 909 comprises creating a set of locations within the vessel that the reference catheter can occupy. This set of locations can then be used during the methods and processes described herein. The purpose of this sampling is to create a set of locations within the system that the reference catheter could move to during a dislodgement scenario. When using the processes and methods described herein, the features of the coronary sinus or other vessel can be taken into account. A vessel comprising unique or non-similar features are useful for the system to determine the location of the reference catheter. A vessel that comprises a homeomorphic structure, such as a spiral, a straight line, a radii of an arc, or multiple spirals can cause a reference catheter with a limited number of data points to not function properly as there are multiple solutions that have the same error or fitness. This can be ameliorated by using an additional features such as including the superior vena cava for additional data points, and using a reference catheter with a larger number of electrodes or other points determinable by a system or device to determine the reference catheter's position that spans the coronary sinus as well as the superior vena cava. By using the superior vena cava for additional data points, at least one additional inflection point can be created in the catheter. In one embodiment, a reference catheter comprising 20 ring electrodes can be used as the reference catheter.

By using the methods and systems described herein, the ability to re-register the mapping and navigation system due to events such as dislodgement or shift/drift is possible. A detected dislodgement of the reference catheter can also be determined independently of other information which may prove valuable to the physician or operator. Further, a distance metric of a target to the input (before registration) can be a potential indicator of shift and/or drift. The algorithms discussed herein can further be used with additional catheters. The additional catheters can comprise both roving catheters and stationary catheters. These additional catheters can comprise coronary sinus catheters, spiral catheters, ablation catheters, and other catheters as would be known to one of ordinary skill in the art. When the processes described herein include the use and registration of roving catheters, the roving catheters can be used to detect shift/drift if the catheter is detected to be outside the geometry defining the cardiac chamber it is contained within. If such catheters enter areas that are not included in the current geometry, this could cause improper re-registration if it was merely an area that was unsampled. This issue can be ameliorated by limiting roving catheters to simple detection of shift/drift using this information to alert the user to acquire additional new geometry or check for the possible occurrence of shift/drift.

While the methods and systems described herein are described as being able to be used with electric field based position and navigations systems, such as "ENSITE NAVX," the methods and systems described herein can further be used in other known technologies for locating/navigating a catheter in space (and for visualization), including for example, the Carto™ visualization and location system available from Biosense Webster, Inc., (e.g., as exemplified by U.S. patent application Ser. No. 08/793,371 (issued as U.S. Pat. No. 6,690,963) hereby incorporated by reference in its entirety as though fully set forth herein), the Aurora™ system available from Northern Digital Inc., a magnetic field based localization system such as that based on the MediGuide™ Technology available from St. Jude Medical, Inc. (e.g., as exemplified by U.S. patent application Ser. No. 09/782,528 (issued as U.S. Pat. No. 7,386,339); U.S. patent application Ser. No. 10/873,409 (issued as U.S. Pat. No. 7,197,354) and U.S. patent application Ser. No. 09/314,474 (issued as U.S. Pat. No. 6,233,476), all of which are hereby incorporated by reference in their entireties as though fully set forth herein) or a hybrid magnetic field-impedance based system, such as the Carto™ 3 visualization and location system available from Biosense Webster, Inc. (e.g., as exemplified by U.S. patent application Ser. No. 12/425,778 (issued as U.S. Pat. No. 7,848,789), which is hereby incorporated by reference in its entirety as though fully set forth herein). Some localization, navigation and/or visualization systems may involve providing a sensor for producing signals indicative of catheter location and/or distal portion orientation information, and can include, for example, one or more electrodes in the case of an impedance-based localization system such as the EnSite™ Velocity™ system running EnSite™ NavX™ software, which electrodes can already exist in some instances, or alternatively, one or more coils (i.e., wire windings) configured to detect one or more characteristics of a low-strength magnetic field, for example, in the case of a magnetic-field based localization system such as one including the MediGuide™ Technology described above. Using the methods and systems described herein in one of these systems can mitigate, control, or reduce shift and/or drift and can detect when a reference catheter is dislodged from a coronary sinus or other vessel where the reference catheter is utilized.

Further, while the systems and methods described herein are used to determine a shape and location of a reference catheter, the systems and methods can be used in other applications. In one embodiment, the systems and methods described herein can be used to merge two images, moving pictures or images, or other visual data. In other embodiments, the systems and methods described herein can be used to collect a point cloud. The point cloud can then be registered to a CT model and fit within the CT model. When using a CT model of a left atrium, the convoluted nature of the geography and shape of the left atrium can be used to fit the information taken to the CT model. In other embodiments, the point cloud can then be registered to a model created through MRI imaging, x-ray imaging, fluoroscopic imaging, infrared imaging, ultrasonic imaging, and combinations thereof.

Although several embodiments have been described above with a certain degree of particularity to facilitate an understanding of at least some ways in which the disclosure may be practiced, those skilled in the art could make numerous alterations to the disclosed embodiments without departing from the scope of the present disclosure and the appended claims. It is intended that all matter contained in the above description or shown in the accompanying drawings shall be interpreted as illustrative only and not limiting. Accordingly, the examples and embodiments herein should not be construed as limiting the scope of the disclosure. Changes in detail or structure may be made without departing from the present teachings. The foregoing description and following claims are intended to cover all such modifications and variations.

Various embodiments are described herein of various apparatuses, systems, and methods. Numerous specific details are set forth to provide a thorough understanding of the overall structure, function, manufacture, and use of the embodiments as described in the specification and illustrated in the accompanying drawings. It will be understood by those skilled in the art, however, that the embodiments may be practiced without such specific details. In other instances, well-known operations, components, and elements may not have been described in detail so as not to obscure the embodiments described in the specification. Those of ordinary skill in the art will understand that the embodiments described and illustrated herein are non-limiting examples, and thus it can be appreciated that the specific structural and functional details disclosed herein may be representative and do not necessarily limit the scope of the embodiments, the scope of which is defined solely by the appended claims.

The terms "including," "comprising" and variations thereof, as used in this disclosure, mean "including, but not limited to," unless express specified otherwise. The terms "a," "an," and "the," as used in this disclosure, means "one or more," unless expressly specified otherwise.

Reference throughout the specification to "various embodiments," "some embodiments," "one embodiment," "an embodiment," or the like, means that a particular feature, structure, or characteristic described in connection with the embodiment is included in at least one embodiment. Thus, appearances of the phrases "in various embodiments," "in some embodiments," "in one embodiment," "in an embodiment," or the like, in places throughout the specification are not necessarily all referring to the same embodiment. Furthermore, the particular features, structures, or characteristics may be combined in any suitable manner in one or more embodiments. Thus, the particular features, structures, or characteristics illustrated or described in connection with one embodiment may be combined, in whole or in part, with the features, structures, or characteristics of one or more other embodiments without limitation.

Although process steps, method steps, algorithms, or the like, may be described in a sequential order, such processes, methods, and algorithms may be configured to work in alternative orders. In other words, any sequence or order of steps that may be described does not necessarily indicate a requirement that the steps be performed in that order. The steps of the processes, methods, and algorithms described herein may be performed in any order practical. Further, some steps may be performed simultaneously.

When a single device or article is described herein, it will be readily apparent that more than one device or article may be used in place of a single device or article. Similarly, where more than one device or article is described herein, it will be readily apparent that a single device or article may be used in place of the more than one device or article. The functionality or the features of a device may be alternatively embodied by one or more other devices which are not explicitly described as having such functionality or features.

It will be appreciated that the terms "proximal" and "distal" may be used throughout the specification with reference to a clinician manipulating one end of an instrument used to treat a patient. The term "proximal" refers to the portion of the instrument closest to the clinician and the term "distal" refers to the portion located furthest from the clinician. However, surgical instruments may be used in many orientations and positions, and these terms are not intended to be limiting and absolute. All other directional or spatial references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

Any patent, publication, or other disclosure material, in whole or in part, that is said to be incorporated by reference herein is incorporated herein only to the extent that the incorporated materials does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material. Based upon the above discussion and illustrations, those skilled in the art will readily recognize that various modifications and changes may be made to the various embodiments without strictly following the exemplary embodiments and applications illustrated and described herein. Such modifications do not depart from the true spirit and scope of various aspects of the disclosure, including aspects set forth in the claims.

What is claimed is:

1. A system for determining one or more characteristics of a device, comprising:
    an electronic control unit configured to:
        initiate an algorithm to correct for shift and drift of a reference catheter;
        determine an initial shape and position of a portion of the reference catheter at first time when the algorithm is initiated;
        determine a current shape and position of the portion of the reference catheter at second time after the algorithm has been initiated, wherein the portion of the reference catheter comprises a plurality of electrodes;
        calculate a closest fit of the current shape and position of the portion of the reference catheter to the initial shape and position of the portion of the reference catheter by iteratively adjusting a set of solution parameters; and
        determine a minimal error solution parameter.

2. The system of claim 1, wherein the electronic control unit is further configured to detect dislodgement of the reference catheter.

3. The system of claim 1, wherein the current shape and position of the portion of the reference catheter comprises a cloud of points.

4. The system of claim 1, wherein the initial shape and position of the portion of the reference catheter comprises one of a shadow, a surface geometry, and a distance map.

5. The system of claim 1, wherein the electronic control is configured to calculate a closest fit by determining a root-mean-square error between the initial shape and position of the portion of the reference catheter and the current shape and position of the portion of the reference catheter.

6. The system of claim 5, wherein the electronic control until is configured to iteratively adjust the set of solution parameters until the root-mean-square error is below a threshold level.

7. The system of claim 6, wherein the threshold level is determined by a user.

8. The system of claim 1, wherein the portion of the reference catheter comprises a length of the catheter within a heart.

9. The system of claim 1, wherein the portion of the reference catheter comprises an entire length of the catheter.

10. The system of claim 1, wherein the electronic control unit is further configured to adjust a set of navigation system coordinates with the minimal error solution parameter.

11. The system of claim 1, wherein the electronic control unit is configured to calculate a closest fit of the current shape and position of the portion of the reference catheter to the initial shape and position of the portion of the reference catheter using an iterative closest point registration.

12. The system of claim 1, wherein the electronic control unit is configured to calculate a closest fit of the current shape and position of the portion of the reference catheter to the initial shape and position of the portion of the reference catheter using a point correspondence.

13. A method for determining one or more characteristics of a device, comprising:
- initiating an algorithm to correct for shift and drift of a reference catheter;
- determining an initial shape and position of a portion of the reference catheter at time 0 when the algorithm is initiated;
- determining a current shape and position of the portion of the reference catheter at time t after the algorithm has been initiated, wherein the portion of the reference catheter comprises a plurality of electrodes;
- calculating a closest fit of the current shape and position of the portion of the reference catheter to the initial shape and position of the portion of the reference catheter by iteratively adjusting a set of solution parameters; and
- determining a minimal error solution parameter.

14. The method of claim 13, further comprising detecting dislodgement of the reference catheter.

15. The method of claim 13, wherein the current shape and position of the portion of the reference catheter comprises a cloud of points.

16. The method of claim 13, wherein the initial shape and position of the portion of the reference catheter comprises one of a shadow, a surface geometry, and a distance map.

17. The method of claim 13, wherein the closest fit is calculated by determining a root-mean-square error between the initial shape and position of the portion of the reference catheter and the current shape and position of the portion of the reference catheter.

18. The method of claim 13, further comprising adjusting a set of navigation system coordinates with the minimal error solution parameter.

19. The method of claim 13, wherein calculating a closest fit of the current shape and position of the portion of the reference catheter to the initial shape and position of the portion of the reference catheter comprises using an iterative closest point registration.

20. The method of claim 13, wherein calculating a closest fit of the current shape and position of the portion of the reference catheter to the initial shape and position of the portion of the reference catheter comprises using a point correspondence.

21. The system of claim 1, wherein the electronic control unit is configured to calculate a closest fit by using a swarm optimization process.

22. The system of claim 21, wherein the swarm optimization process comprises an iterative point based method.

23. The system of claim 21, wherein the swarm optimization process comprises a method of evolutionary computing.

24. The system of claim 1, wherein the electronic control unit is configured to use a slow update method.

25. The system of claim 1, wherein the electronic control unit is configured to use a fast update method.

* * * * *